United States Patent [19]

Coolbaugh et al.

[11] Patent Number: 5,510,548
[45] Date of Patent: Apr. 23, 1996

[54] VULCANIZABLE LIQUID COMPOSITIONS

[75] Inventors: Thomas S. Coolbaugh, Morrisville; Frederick C. Loveless, Yardley, both of Pa.; Demetreos N. Matthews, Ewing; Leslie R. Rudnick, Lawrenceville, both of N.J.

[73] Assignee: Mobil Oil Corporation, Fairfax, Va.

[21] Appl. No.: 443,741

[22] Filed: May 18, 1995

Related U.S. Application Data

[62] Division of Ser. No. 382,814, Feb. 3, 1995.

[51] Int. Cl.$^6$ .............................. C07C 2/40; C08F 297/04
[52] U.S. Cl. .............................. 585/12; 585/10; 585/17; 585/24; 585/507; 526/337; 526/340
[58] Field of Search ..................... 585/12, 10, 17, 585/24, 507; 526/337, 340

[56] References Cited

U.S. PATENT DOCUMENTS

| | | | |
|---|---|---|---|
| 3,607,982 | 9/1971 | Winkler et al. | 525/314 |
| 3,766,215 | 10/1973 | Hesse et al. | 526/337 |
| 3,795,615 | 3/1974 | Pappas et al. | 252/59 |
| 4,413,098 | 11/1983 | Hattori et al. | 525/314 |
| 4,501,857 | 2/1985 | Kishimoto et al. | 525/338 |
| 4,843,120 | 6/1989 | Halasa et al. | 526/173 |
| 4,879,349 | 11/1989 | Hoxmeier | 525/314 |

FOREIGN PATENT DOCUMENTS

| | | | |
|---|---|---|---|
| 0315280 | 5/1989 | European Pat. Off. . | |
| 56-127604 | 10/1981 | Japan | 526/337 |
| 328729 | 7/1989 | Japan . | |
| 2020670 | 11/1979 | United Kingdom | 585/507 |

OTHER PUBLICATIONS

Falk, Journal of Polymer Science: Part A–1, vol. 9, 2617–2623 (1971).
Falk et al., Die Angewandte Makromelekulare Chemie 21 (1972), 17–23 (No.236).
Mohajer et al., Polymer, 1982, vol. 23, Sep., 1523–1535.

*Primary Examiner*—Ponnathapura Achutamurthy
*Attorney, Agent, or Firm*—A. J. McKillop; M. D. Keen

[57] ABSTRACT

There is disclosed a linear block copolymer comprising at least one triblock I-B-I, wherein I is a block of at least one polymerized conjugated diene of at least five (5) carbon atoms, such as isoprene, and B is a block of a polymer of at least one conjugated diene, different from that used to polymerize the block I, of at least four (4) carbon atoms, such as 1,3-butadiene. The B block is selectively hydrogenated, while each of the I blocks is unhydrogenated and therefore retains a sufficient amount of its original unsaturation to vulcanize the copolymer. There is also disclosed an alternative linear block copolymer containing at least one triblock of the first polymer block made from a minor proportion of at least one aryl-substituted olefin, such as styrene, and a major proportion of at least one conjugated diene used to polymerize the block I, the second middle polymer block of at least one diene used to polymerize the block B, and the third polymer block which is the same as the first polymer block. In this alternative copolymer, the middle block is also selectively hydrogenated, thereby leaving the terminal polymer blocks with a sufficient amount of their original unsaturation to vulcanize the copolymer. The polymers can be crosslinked or functionalized through the terminal blocks containing the vinyl unsaturation. There are also disclosed random linear and star-branched block and random copolymers made from the same monomers as the linear block copolymers.

Also disclosed are methods of producing the polymers and selectively hydrogenating the aforementioned polymerized dienes.

27 Claims, 2 Drawing Sheets

VULCANIZABLE LIQUID COMPOSITIONS

CROSS-REFERENCE TO RELATED APPLICATIONS

This is a division of application Ser. No. 08/382,814, filed on Feb. 3, 1995.

This application is related by subject matter to application Ser. No. 07/466,233 filed on Jan. 16, 1990, now U.S. Pat. No. 5,187,236 and to application Ser. No. 07/466,136 filed on Jan. 16, 1990.

The entire contents of application Ser. No. 07/466,136, filed on Jan. 16, 1990 are incorporated herein by reference).

BACKGROUND OF THE INVENTION

1. Field of the Invention

This invention is directed to novel liquid block copolymers having unsaturation only on the terminal blocks and methods of preparation thereof. More particularly, the invention is directed to liquid block copolymers comprising triblock units wherein the middle block of each triblock unit is substantially selectively hydrogenated and therefore contains substantially no unsaturated groups, while each of the terminal blocks of each triblock unit contains a sufficient amount of unsaturation for curing the block copolymers.

The invention is also directed to random liquid copolymers which, when selectively hydrogenated, contain molecules having substantially saturated backbones and random, pendant unsaturation.

The invention is additionally directed to chemically modified derivatives of the above block and random copolymers.

Crosslinking of the polymers of the invention produces elastomeric vulcanizates having unusual properties, e.g., high elongation and excellent aging characteristics.

2. Description of Related Art

Elastomers (or rubbers) of either natural or synthetic origin usually require vulcanization for transformation into insoluble, high strength elastomeric products. Before vulcanization, rubbers possess inferior properties and low strength which limit their utility.

There are a number of well known methods for achieving the vulcanization, also referred to as crosslinking, of unsaturated elastomers. Such methods include the use of sulfur and accelerators, peroxides, benzoquinone dioxime, certain phenolic resins and similar agents. Any of the above or any other well known vulcanizing techniques may be utilized to crosslink the elastomers of this invention.

Liquid elastomers are well known and are used in various applications. For example, many functionally terminated polybutadiene liquid elastomers are known. These materials are generally highly unsaturated and frequently form the base polymer for polyurethane formulations. The preparation and application of hydroxy-terminated polybutadiene is detailed by J. C. Brosse et al in HYDROXYL-TERMINATED POLYMERS OBTAINED BY FREE RADICAL POLYMERIZATION—SYNTHESIS, CHARACTERIZATION AND APPLICATIONS, ADVANCES IN POLYMER SCIENCE 81, Springer-Verlag, Berlin Heidelberg, 1987, pp 167–220.

Also, liquid polymers possessing acrylate, carboxy- or mercapto-terminals are known. In addition to butadiene, it is known to utilize isoprene as the base monomer for the liquid elastomers. The liquid elastomers may contain additional monomers, such as styrene or acrylonitrile, for controlling compatibility in blends with polar materials, such as epoxy resins.

Also known in the prior art are pure hydrocarbon, non-functionalized liquid rubbers. These liquid elastomers contain varying degrees of unsaturation for utilization in vulcanization. Typical of highly unsaturated liquid elastomers is polybutadiene, e.g., that sold under the name RICON by Colorado Chemical Specialties Co. A liquid polyisoprene which has been hydrogenated to saturate 90% of its original double bonds is marketed as LIR-290 by Kuraray Isoprene Chemical Co. Ltd. Still more highly saturated are liquid butyl rubbers available from Hardman Rubber Co., and Trilene, a liquid ethylene—propylene—diene ruber (EPDM) from Uniroyal Chemical Co. The more highly saturated liquid elastomers exhibit good oxidation and ozone resistant properties. The above prior art liquid elastomers, with either high or low levels of unsaturation, are characterized in that, having random unsaturation, they are randomly crosslinked during vulcanization. The success of vulcanization in incorporating all molecular chains into the final crosslinked network with minimal "loose ends" is termed the degree of network perfection. An imperfect network, wherein crosslinks occur randomly and sometimes not near the end of a molecular chain, produces a vulcanized polymer having poor mechanical and elastomeric properties caused by chain ends which are not a part of the tightly bound network. In order to insure the highest degree of network perfection attainable, randomly unsaturated elastomers must be crosslinked extensively. The large number of crosslinks necessary dictates that the average distance between crosslinks ($M_c$) must be relatively small in comparison with the dimensions of the whole molecule. Elastomeric properties, such as elongation, depend greatly on $M_c$—the smaller the $M_c$ the worse are the elastomeric properties, e.g., the lower the elongation of the polymer.

Falk, JOURNAL OF POLYMER SCIENCE: PART A-1, Volume 9, 2617–2623 (1971), the entire contents of which are incorporated herein by reference, discloses a method of selectively hydrogenating 1,4,-polybutadiene in the presence of 1,4-polyisoprene. More particularly, Falk discloses selective hydrogenation of the 1,4-polybutadiene block segment in the block copolymer of 1,4-polybutadiene-1,4-polyisoprene-1,4-polybutadiene and in random copolymers of butadiene and isoprene, with both polymerized monomers having predominantly 1,4-microstructure. Selective hydrogenation is conducted in the presence of hydrogen and a catalyst made by the reaction of organoaluminium or lithium compounds with transition metal salts of 2-ethylhexanoic acid.

Falk, DIE ANGEWANDTE CHEMIE 21 (1972) 17–23 (No. 286), the entire contents of which are also incorporated herein by reference, discloses the selective hydrogenation of 1,4-polybutadiene segments in a block copolymer of 1,4-polybutadiene-1,4-polyisoprene-1,4-polybutadiene.

Hoxmeier, Published European Patent Application 88202449.0, filed on Nov. 2, 1988, Publication Number 0 315 280, published on May 10, 1989, discloses a method of selectively hydrogenating a polymer made from at least two different conjugated diolefins. One of the two diolefins is more substituted in the 2,3 and/or 4 carbon atoms than the other diolefin and produces tri- or tetra-substituted double bond after polymerization. The selective hydrogenation is conducted under such conditions as to hydrogenate the ethylenic unsaturation incorporated into the polymer from the lesser substituted conjugated diolefin, while leaving unsaturated at least a portion of the tri- or tetra-substituted unsaturation incorporated into the polymer by the more substituted conjugated diolefin.

Mohajer et al, *Hydrogenated Linear Block Copolymers of Butadiene and Isoprene: Effects of Variation of Composition and Sequence Architecture on Properties*, 23 POLYMER 1523–1535 (Sept. 1982) disclose essentially completely hydrogenated butadiene-isoprene-butadiene (HBIB), HIBI and HBI block copolymers in which butadiene has predominantly 1,4-microstructure.

Kuraray K K, Japanese published patent application Number JP-328 729, filed on Dec. 12, 1987, published on Jul. 4, 1989, discloses a resin composition comprising 70–99% wt. of a polyolefin (preferably polyethylene or polypropylene) and 1–30% wt. of a copolymer obtained by hydrogenation of at least 50% of unsaturated bond of isoprene/butadiene copolymer.

Heretofore, the art has failed to produce liquid hydrocarbon elastomers having the capability of maintaining relatively large distance between cross-links (high $M_c$) after vulcanization.

Accordingly, it is an object of this invention to provide liquid polymers capable of being vulcanized to a substantially perfect network with a distance between crosslinks nearly equivalent to the dimensions of the unvulcanized elastomeric molecule. In addition to the expected improvements in elastomeric properties, the unperturbed saturated main chain of the polymers of this invention provides a high degree of oxidative and thermal stability. Unique materials can also be obtained by chemical modification of the polymers of this invention since the polymers of the invention can be selectively modified at the terminal ends of the molecules.

It is an additional object of this invention to provide a method for the production of random copolymers having controlled amounts of unsaturation incorporated randomly in an otherwise saturated backbone. In contrast to EPDM, the level of unsaturation can be inexpensively and easily controlled, e.g., from 1% to 50%, to provide a wide variation in vulcanization rate and potential co-curability with various highly unsaturated rubbers based on butadiene or isoprene.

SUMMARY OF THE INVENTION

In one embodiment of the invention, there is provided a liquid block copolymer comprising at least three alternating blocks:

$$(I)_x\text{-}(B)_y\text{-}(I)_x$$

wherein

I is a block of at least one polymerized conjugated diene having at least five (5) carbon atoms and the following formula $$R^1-C=C-C=C-R^6 \quad (1)$$
$$\quad\ |\ \ \ |\ \ \ |\ \ \ |$$
$$\quad R^2\ R^3\ R^4\ R^5$$

wherein $R^1$–$R^6$ are each hydrogen or a hydrocarbyl group, provided that at least one of $R^1$–$R^6$ is a hydrocarbyl group and further provided that the structure of the residual double bond in the polymerized block I has the following formula $$R^{II} \quad (2)$$
$$\ |$$
$$R^{I}-C=C-R^{III}$$
$$\quad\quad\ |$$
$$\quad\ R^{IV}$$

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups; B is a block of a polymer of at least one conjugated diene, different from that used to polymerize the I block, having at least four (4) carbon atoms and the following formula $$R^7-C=C-C=C-R^{12} \quad (3)$$
$$\quad\ |\ \ \ |\ \ \ |\ \ \ |$$
$$\quad R^8\ R^9\ R^{10}\ R^{11}$$

wherein $R^7$–$R^{12}$ are each hydrogen or a hydrocarbyl group, provided that the structure of the residual double bond in the polymerized conjugated diene of formula (3) (block B) has the following formula $$R^b \quad (4)$$
$$\ |$$
$$R^a-C=C-R^c$$
$$\quad\quad\ |$$
$$\quad\ R^d$$

wherein $R^a$, $R^b$, $R^c$ and $R^d$ are each hydrogen (H) or a hydrocarbyl group, provided that one of $R^a$ or $R^b$ is hydrogen, one of $R^c$ or $R^d$ is hydrogen and at least one of $R^a$, $R^b$, $R^c$ or $R^d$ is a hydrocarbyl group;

x is at least 1, preferably 1 to 30, more preferably 2 to 20, and most preferably 3 to 10, and y is at least 25, preferably 30 to 275, more preferably 85 to 225, and most preferably 130 to 200. It will be apparent to those skilled in the art that in the residual double bond of formula (2), $R^I$, $R^{II}$, $R^{III}$ and $R^{IV}$ may all be hydrocarbyl groups.

The hydrocarbyl group or groups in the formulae (1) and (2) are the same or different and they are substituted or unsubstituted alkyl, alkenyl, cycloalkyl, cycloalkenyl, aryl, alkaryl or aralkyl groups or any isomers thereof. Examples of suitable conjugated dienes used to polymerize the I block are isoprene, 2,3-dimethyl butadiene, 2-methyl-1,4-pentadiene or myrcene. The hydrocarbyl groups in formulae (3) and (4) are the same as those described above in conjunction with the discussion of formulae (1) and 2. Suitable conjugated dienes used to polymerize the B block are 1,3-butadiene or 1,3-pentadiene. After the polymerization is completed, the block polymer is hydrogenated so that the block B is selectively hydrogenated to such an extent that it contains substantially none of the original unsaturation, while each of the blocks I retains a sufficient amount of its original unsaturation to cure (or vulcanize) the block copolymer. The block copolymer is terminated at both ends with a block I.

In an alternative embodiment, there is provided a block copolymer comprising at least three alternating blocks:

$$(A)_x\text{-}(D)_y\text{-}(A)_x$$

wherein the block A is a block or random copolymer of about 30 to about 70%, preferably about 40 to about 60%, by mole of at least one aryl-substituted olefin, such as styrene, 2-phenyl alpha-olefins, alkylated styrene, vinyl naphthalene or alkylated vinyl naphthalene, and about 30 to about 70, preferably about 40 to 60%, by mole of at least one conjugated diene of formula (1), discussed above; D is a block of a polymer of at least one conjugated diene of formula (3), discussed above, which is different from the conjugated diene of formula (1) used to polymerize the block (A); x is about 2 to about 30%, preferably about 4 to about 16%, by wt., of the weight of the triblock copolymer, and y is about 40 to about 96%, preferably about 68 to about 92%, by wt., of the weight of the triblock copolymer. Examples of suitable conjugated dienes used to polymerize the A block are isoprene, 2,3-dimethyl butadiene, myrcene or 2-methyl-1,3-pentadiene. Suitable conjugated dienes used to polymerize the D block are 1,3-butadiene or 1,3-pentadiene.

After this block copolymer is polymerized, it is hydrogenated, so that the block D is selectively hydrogenated to such an extent that it contains substantially none of the original unsaturation, while each of the blocks A retains a sufficient amount of the original unsaturation of the conjugated diene present in each of the A blocks to cure the block copolymer. The block copolymer of this embodiment is terminated at both ends with a block A.

The blocks A and I are referred to hereinafter as the "terminal blocks", and the blocks B and D as the "middle blocks".

Yet another embodiment is directed to a block copolymer comprising at least three alternating blocks:

I-D-A wherein the blocks I, D and A are polymerized from the same monomers as discussed above for the respective blocks. The block copolymer comprises about 1 to about 15, preferably about 2 to about 8% wt. of the block I, about 2 to about 30, preferably about 4 to about 16% wt. of the blocks A and about 55 to about 97, preferably about 76 to about 94% wt. of the blocks D. The block A of this copolymer is either a block or a random copolymer of about 30 to about 70% by mole of at least one aryl-substituted olefin and about 30 to about 70% by mole of at least one conjugated diene of formula (1).

Another embodiment of the invention is directed to random copolymers of at least one conjugated diene of formula (1) and at least one conjugated diene of formula (3), both discussed above, provided that the diene of formula (3) is different from the diene of formula (1). This random copolymer contains about 1.0 to about 25, preferably about 1.0 to about 10% by mole of the polymerized conjugated diene of formula (1) and about 75 to about 99%, preferably about 90 to 99% by mole of the conjugated diene of formula (3). This random copolymer is also selectively hydrogenated, so that the polymerized diene of formula (3) contains none of the original unsaturation, while the polymerized diene of formula (1) retains a sufficient amount of the original unsaturation to cure the random copolymer.

Another embodiment of this invention is directed to random copolymers of at least one aryl-substituted olefin, at least one conjugated diene of formula (1) and at least one conjugated diene of formula (3), both discussed above, provided that the conjugated diene of formula (1) is different from the conjugated diene of formula (3). This random copolymer contains about 0.3 to about 15% by mole of the aryl-substituted olefin, about 1.0 to about 25%, preferably about 1.0 to about 10%, by mole of the conjugated diene of formula (1), and the remainder of the conjugated diene of formula (3). This random copolymer is also hydrogenated, so that the polymerized diene of formula (3) is selectively hydrogenated to such an extent that it contains none of the original unsaturation, while the polymerized diene of formula (1) retains a sufficient amount of the original unsaturation to cure the random copolymer.

Yet another embodiment of the invention is directed to star-branched block and random polymers. The star-branched block polymers are made from any combination of blocks I and B, A and D, or I, D and A, providing that each free end (i.e., uncoupled end) of the star-branched polymer is either an I or an A block, respectively. The star-branched block polymers are selectively hydrogenated to such an extent that blocks B or D contain substantially none of the original unsaturation, while each of the blocks I or A, respectively, retains a sufficient amount of the original unsaturation of the conjugated dienes present therein to cure the star-branched block polymers.

The star-branched random polymers are made from any combination of dienes of formulae (1) and (3), providing that the diene of formula (1) is different from the diene of formula (3), or from at least one aryl-substituted olefin, at least one diene of formula (1) and at least one diene of formula (3), providing that the diene of formula (3) is different from the diene of formula (1). The star-branched random polymers are selectively hydrogenated, so that the polymerized diene of formula (3) contains none of the original unsaturation, while the polymerized diene of formula (1) retains a sufficient amount of the original unsaturation to cure the star-branched random polymers.

The copolymers of all embodiments are prepared under anionic polymerization conditions. After the selective hydrogenation reaction, the hydrogenation catalyst is removed from the polymer.

In all embodiments of this invention, whenever a reference is made to the "residual double bond" of the block or random polymer (or copolymer), it is understood to be the residual double bond prior to the hydrogenation reaction. The structure of the residual double bond can be determined in any conventional manner, as is known to those skilled in the art, e.g., by infrared (IR) or NMR analysis.

The term "original unsaturation", as used herein, means the sum total of the unsaturated groups present in all blocks of the copolymer prior to the selective hydrogenation reaction. The unsaturation can be quantified in any conventional manner, e.g., by reference to the Iodine Number of the polymer. For example, for a block copolymer of the first embodiment wherein the I blocks are polyisoprene and the B block is polybutadiene, the Iodine Number before selective hydrogenation for each of the I blocks is 373 and for the B block it is 470. After selective hydrogenation is completed, the Iodine Number for each of the I blocks is about 75 to about 373, and for the B block it is about 0 to about 50, preferably about 0 to about 2.5 and most preferably about 0 to about 1.

In any polymers of any of the embodiments of this invention, the microstructure of the polymerized conjugated diene of formula (3), e.g., blocks B or D in the block copolymers, must be such that the polymer is not excessively crystalline after the selective hydrogenation reaction, i.e., after the selective hydrogenation reaction the polymer must retain its elastomeric properties e.g., the polymer should contain not more than about 10% of polyethylene crystallinity. This is accomplished by introducing side branches into the polymerized conjugated diene of formula (3), e.g., by controlling the microstructure of 1,3-butadiene if it is the predominant monomer in the diene of formula (3), by using a mixture of dienes of formula (3) containing less than predominant amounts of 1,3-butadiene or by using a single diene of formula (3), other than 1,3-butadiene. More particularly, if the conjugated diene(s) of formula (3) is predominantly (at least 50% by mole) 1,3-butadiene, the side branches are introduced into the polymer by insuring that the polymerized diene of formula (3) contains a sufficient amount of the 1,2-units to prevent the selectively hydrogenated polymer from being excessively crystalline. Thus, if the conjugated diene of formula (3) is predominantly (at least 50% by mole, e.g., 100% by mole) 1,3-butadiene, the polymerized diene of formula (3), prior to the selective hydrogenation reaction, must contain not more than about 75% wt., preferably about 10 to about 70% wt., and most preferably about 35 to about 55% wt. of the 1,4-units, and at least about 25% wt., preferably about 30 to about 90% wt., and most preferably about 45 to about 65% wt. of the 1,2-units. If the polymerized diene(s) of formula (3) contains less than 50% by mole of formula (3), 1,3-butadiene, e.g., 1,3-pentadiene is used as the only diene of the microstructure of the polymerized diene of formula (3) prior to the selective hydrogenation reaction is not critical since, after hydrogenation, the resulting polymer will contain substantially no crystallinity.

In all embodiments of the invention, mixtures of dienes of formulae (1) or (3) may be used to prepare block copolymers $(I)_x-(B)_y-(I)_x$, $(A)_x-(D)_y-(A)_x$ or I-D-A, any of the random copolymers or star-branched block and random polymers of the invention. Similarly, mixtures of aryl-substituted olefins may also be used to prepare block, random or star-branched copolymers of this invention. Accordingly, whenever a reference is made herein to a diene of formulae (1) or (3), or to an aryl-substituted olefin, it may encompass more than one diene of formulae (1) or (3), respectively, and more than one aryl-substituted olefin.

DETAILED DESCRIPTION OF THE INVENTION

Figure 1:
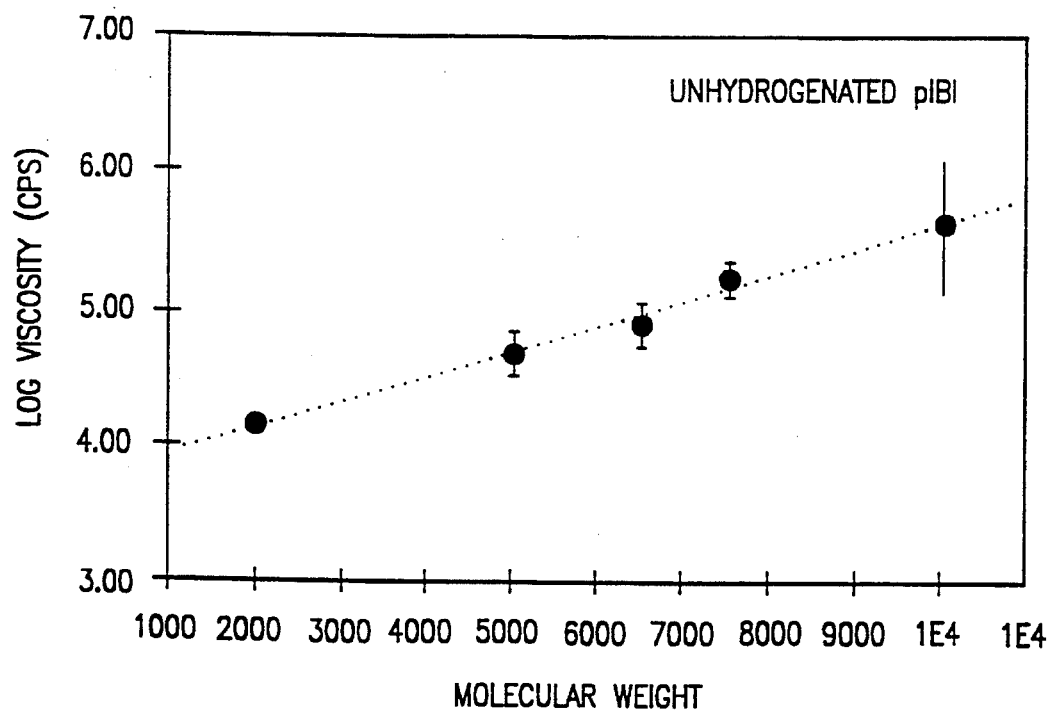
FIG. 1 shows the relationship of viscosity as a function of molecular weight for the unhydrogenated isoprene-butadiene-isoprene triblock polymer of this invention.

The block copolymers of this invention comprise three or more alternating blocks, identified above. Linear block copolymers having more than three blocks are contemplated herein, although they do not appear to exhibit better properties than the block copolymers containing only three blocks. However, star-branched block polymers containing any combination and number of blocks I and B, A and D, or I, D and A are also contemplated herein, providing that they are terminated either by blocks I or A, respectively. The central (middle) block of each linear three block unit is substantially completely saturated, while the terminal blocks contain controlled levels of unsaturation providing a hydrocarbon elastomer with α-ω unsaturation. The length of the central saturated block defines the distance between crosslinks ($M_c$) in the vulcanized elastomers. Because of the α-ω placement of the unsaturation, very low levels of residual double bonds are required to attain excellent vulcanization. The low level of unsaturation in the selectively hydrogenated triblock polymer and its terminal positioning provide excellent oxidative stability to the polymers of this invention.

Without wishing to be bound by any theory, it is believed that the α-ω placement of unsaturation in the polymers of this invention imparts to the polymers excellent elastomeric properties which were absent in prior art thermosetting liquid elastomers which required a multiplicity of relatively closely spaced crosslinks.

The combination of elastomeric properties and oxidative stability possessed by the polymers of this invention makes them suitable for many end uses, such as sealants, caulks and adhesives.

Many variations in composition, molecular weight, molecular weight distribution, relative block lengths, microstructure, branching and Tg (glass transition temperature) attainable with the use of anionic techniques employed in the preparation of our polymers will be obvious to those skilled in the art.

While not wishing to limit the molecular weight range of liquid elastomers prepared according to our invention, the minimum molecular weight for these liquid polymers is at least about 2,000, preferably about 5,000 to about 15,000, and most preferably about 7,500 to about 10,000. Star-branched block and random polymers of this invention may have substantially higher molecular weights and still retain liquid properties. For example, liquid star-branched block polymers having molecular weight of about 34,000 have been prepared. The block copolymers of this invention are vulcanizable. Without wishing to be bound by any theory of operability, it is believed that they can be crosslinked (or vulcanized) in a controlled manner through the unsaturated groups on the terminal blocks to provide a very strong and orderly matrix of crosslinkages having almost uniform distribution of molecular weights between crosslinks, $M_c$. The random and star-branched copolymers of this invention are also vulcanizable. The designation $M_c$, as used herein for the block copolymers means the length of the middle block. For random copolymers, $M_c$ is calculated by dividing number average molecular weight, $M_n$, of the polymer by the average number of crosslinks per chain plus 1.

The invention will be described hereinafter in terms of the embodiments thereof summarized above. However, it will be apparent to those skilled in the art, that the invention is not limited to these particular embodiments, but, rather, it covers all the embodiments encompassed by the broadest scope of the description of the invention.

Liquid Block Copolymers From at Least Two Dissimilar Conjugated Dienes

In this embodiment of the invention, there is polymerized a block copolymer comprising at least three alternating blocks:

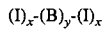

wherein:

I is a block of at least one polymerized conjugated diene having at least five (5) carbon atoms and the following formula

wherein $R^1-R^6$ are each hydrogen or a hydrocarbyl group, provided that at least one of $R^1-R^6$ is a hydrocarbyl group, and further provided that the structure of the residual double bond in the polymerized block I has the following formula

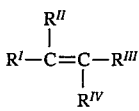

(2)

wherein

R$^I$, R$^{II}$, R$^{III}$ and R$^{IV}$ are each hydrogen or a hydrocarbyl group, provided that either both R$^I$ and R$^{II}$ are hydrocarbyl groups or both R$^{III}$ and R$^{IV}$ are hydrocarbyl groups;

B is a block of at least one polymerized conjugated diene, different from that used to polymerize block I, having at least four (4) carbon atoms and the following formula

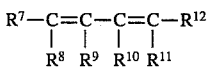

(3)

wherein

R$^7$–R$^{12}$ are each hydrogen or a hydrocarbyl group, provided that the structure of the residual double bond in the polymerized block B has the following formula

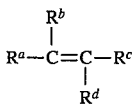

(4)

wherein

R$^a$, R$^b$, R$^c$ and R$_d$ are each hydrogen (H) or a hydrocarbyl group, provided that one of R$^a$ or R$^b$ is hydrogen, one of R$^c$ or R$^d$ is hydrogen and at least one of R$^a$, R$^b$, R$^c$ R$^d$ is a hydrocarbyl group;

x is at least 1, preferably 1 to 15, more preferably 2 to 10, and most preferably 2 to 7, y is at least 25, preferably 90 to 300, more preferably 130 to 200, and most preferably 140 to 200. The above definition of x means that each of the I blocks is polymerized from at least 1, preferably from 1–15, more preferably from 2–10 and most preferably from 2–7 monomer units. For some special applications, each of the I blocks is polymerized from 20–30 monomer units. The block polymers containing such large I blocks have increased vulcanization rate, as compared to those containing smaller I blocks, and are co-vulcanizable with diene rubbers available in the art, e.g., polybutadiene and natural rubbers. The block polymers containing such large I blocks can be blended with diene rubbers by conventional methods and subsequently vulcanized to produce novel compositions of this invention. The resulting materials are expected to have increased oxidation and ozone degradation resistance as compared to known diene rubbers alone, and therefore are expected to be valuable materials for the production of white sidewalls of tires and similar articles.

Similarly, the above definition of y means that each of the B blocks is polymerized from at least 25, preferably from 90 to 300, more preferably from 130 to 200, and most preferably from 140 to 200 monomer units. In the residual double bond of formula (2), R$^I$, R$^{II}$, R$^{III}$ and R$^{IV}$ may all be hydrocarbyl groups.

The structures of the residual double bonds defined by formulae (2) and (4) are necessary to produce copolymers which can be selectively hydrogenated in the manner described herein, to produce the selectively hydrogenated block and random copolymers of this invention.

The block copolymer comprises about 0.5 to about 25%, preferably about 1 to about 5% by wt. of the I blocks, and about 75 to about 99.5%, preferably about 95 to about 99% by wt. of the B blocks.

The hydrocarbyl group or groups in the formulae (1) and (2) are the same or different and they are substituted or unsubstituted alkyl, alkenyl, cycloalkyl, cycloalkenyl, aryl, alkaryl or aralkyl groups or any isomers thereof. Suitable hydrocarbyl groups are alkyls of 1–20 carbon atoms, alkenyls of 1–20 carbon atoms, cycloalkyls of 5–20 carbon atoms, cycloalkenyls of 5–20 carbon atoms, aryls of 6–12 carbon atoms, alkaryls of 7–20 carbon atoms or aralkyls of 7–20 carbon atoms. Examples of suitable alkyl groups are methyl, ethyl, propyl, butyl, pentyl, hexyl, heptyl, octyl, decyl, methyl-decyl or dimethyl-decyl. Examples of suitable alkenyl groups are ethenyl, propenyl, butenyl, pentenyl or hexenyl. Examples of suitable cycloalkyl groups are cyclohexyl or methylcyclohexyl. Examples of suitable cycloalkenyl groups are 1-, 2-, or 3-cyclohexenyl or 4-methyl-2-cyclohexenyl. Examples of suitable aryl groups are phenyl or diphenyl. Examples of suitable alkaryl groups are 4-methyl-phenyl (p-tolyl) or p-ethyl-phenyl. Examples of suitable aralkyl groups are benzyl or phenethyl. Suitable conjugated dienes of formula (1) used to polymerize the I block are isoprene, 2,3-dimethyl-butadiene, 2-methyl-1,3-pentadiene, myrcene, 3-methyl-1,3-pentadiene, 4-methyl-1,3-pentadiene, 2-phenyl-1,3-butadiene, 2-phenyl-1,3-pentadiene, 3-phenyl-1,3-pentadiene, 2,3-dimethyl-1,3-pentadiene, 2-hexyl-1,3-butadiene, 3-methyl-1,3-hexadiene, 2-benzyl-1,3-butadiene, 2-p-tolyl-1,3-butadiene or mixtures thereof, preferably isoprene, myrcene or 2-methyl-1,3-pentadiene, and most preferably isoprene.

The hydrocarbyl group or groups in the formula (3) may or may not be the same as those in formula (4). These hydrocarbyl groups are the same as those described above in conjunction with the discussion of the hydrocarbyl groups of formulae (1) and (2). Suitable monomers for the B block are 1,3-butadiene, 1,3-pentadiene, 2,4-hexadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene or mixtures thereof, preferably 1,3-butadiene, 1,3-pentadiene, 2,4-hexadiene or 1,3-hexadiene, and most preferably it is 1,3-butadiene. It is preferred that each of the B blocks is polymerized from a single monomer.

The block copolymer of this embodiment is terminated at both ends with a block I.

The scope of this embodiment, and of any other embodiments of the invention wherein the block B is used, also encompasses polymers wherein the central block B may comprise copolymers of one or more conjugated diene of formula (3) and controlled amounts (about 0.3 to about 30 mole %) of an aryl-substituted olefin, e.g., styrene or other suitable monomers (such as alkylated styrene, vinyl napthalene or alkylated vinyl naphthalene) incorporated for control of glass transition temperature (Tg), density, solubility parameters and refractive index. Suitable aryl-substituted olefins are those described below in conjunction with the second embodiment of the invention. Similarly, the scope of this embodiment also encompasses polymers wherein the central block B may be comprised of copolymers of one or more conjugated diene of formula (3) and any other anionically polymerizable monomer capable of polymerizing with the conjugated diene of formula (3).

It will be apparent to those skilled in the art that proper choice of polymerization parameters can produce polymers with a great variety of compositional and structural differences, falling within the scope of our invention. Changes in composition of the central block B control the nature of the rubbery properties while changes in the terminal blocks permit response to different vulcanizing agents, e.g., quinone dioxime, sulfur-based and phenolic resin cure systems.

The block copolymer is polymerized by any conventional block copolymerization process, such as anionic polymerization, discussed in detail below. As will be apparent to those skilled in the art, the copolymer of this embodiment contains at least three alternating blocks, I-B-I, referred to herein as the triblocks or triblock units, but it may contain an unlimited number of blocks, so long as the entire block copolymer is terminated at both ends by the I blocks. Polymers having more than three blocks (such as five) allow crosslinking to take place at the ends and in the central portion, but maintain a controlled large distance between crosslinks. It is important to have the block copolymer terminated at each end with the I blocks to assure that there are unsaturated groups at each end of the block copolymer enabling the block copolymer to be cross-linked or functionalized at the terminal ends thereof. The term "functionalized" is used herein to describe chemical modifications of the unsaturated groups to produce functional groups, the nature of which is described in detail below. The crosslinking of the functionalized and nonfunctionalized copolymer chains is conducted in a conventional manner and is described below.

After the block copolymer is polymerized, it is subjected to a selective hydrogenation reaction during which the B blocks of the block copolymer are selectively hydrogenated to such an extent that they contain substantially none of the original unsaturation, while the I blocks retain a sufficient amount of their original unsaturation to cure the block copolymer. Generally, for a block copolymer wherein the I and B blocks are polymerized from any of the monomers discussed above, the Iodine Number for the I blocks after the selective hydrogenation reaction is about 20 to about 100%, preferably about 50 to about 100%, and most preferably about 100% of the Iodine Number prior to the selective hydrogenation reaction and for the B blocks it is about 0 to about 10%, preferably about 0 to about 0.5%, and most preferably about 0 to about 0.2% of the Iodine Number prior to the selective hydrogenation reaction. The Iodine Number, as is known to those skilled in the art, is defined as the theoretical number of grams of iodine which will add to the unsaturation in 100 grams of olefin and is a quantitative measure of unsaturation.

In this embodiment of the invention, although the microstructure of the I blocks is not critical and may consist of 1,2-, 3,4- and/or 1,4-units, schematically represented below for the polyisoprene blocks, when a polar compound is used during the polymerization of the I block, the I blocks comprise primarily (at least about 80% wt.) 3,4-units, the rest being primarily (about 20% wt.) 1,2-units; when the polar compound is not used during the polymerization of the I block, the I blocks comprise primarily (about 80% wt.) 1,4-units, the rest being primarily 1,2- and 3,4-units.

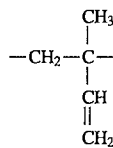  1,2

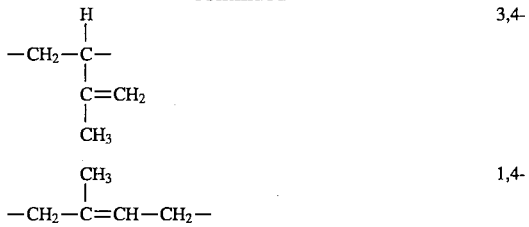

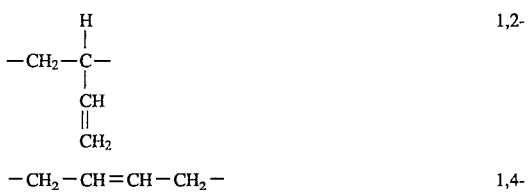

The microstructure of the B blocks, when the predominant monomer used to polymerize the B blocks is 1,3-butadiene, should be a mixture of 1,4- and 1,2-units schematically shown below for the polybutadiene blocks:

$$-CH_2-\underset{\underset{CH_2}{\overset{\|}{CH}}}{\overset{H}{C}}- \quad 1,2-$$

$$-CH_2-CH=CH-CH_2- \quad 1,4-$$

since the hydrogenation of the predominantly 1,4-microstructures produces a crystalline polyethylene segment. The microstructure of the I and B blocks (as well as of the polymerized conjugated dienes of formulae (1) or (3) in any polymers of this invention) is controlled in a conventional manner, e.g., by controlling the amount and nature of the polar compounds used during the polymerization reaction, and the reaction temperature. In one particularly preferred embodiment, the B block contains about 50% of the 1,2- and about 50% of the 1,4-microstructure. If the B block is poly-1,3-butadiene, the hydrogenation of the B segment containing about 50 to about 60% of the 1,2-microstructure content produces an elastomeric center block which is substantially an ethylene-butene-1 copolymer having substantially no crystallinity. If the B block is polymerized from 1,3-pentadiene, it is preferred that it have predominantly (at least 50%) of 1,4-microstructure which, after hydrogenation, produces a substantially non-crystalline elastomeric block.

The terms 1,2-, 1,4-, and 3,4-microstructure or units as used in this application refer to the products of polymerization obtained by the 1,2-, 1,4- and 3,4-, respectively, additions of two monomer units.

We surprisingly discovered that the polymerized conjugated dienes of formula (3), e.g., the B blocks, of the polymers of this invention are selectively hydrogenated in our hydrogenation process much faster than the polymerized conjugated dienes of formula (1), e.g., the I blocks. This is not evident from the teachings of Falk, discussed above, because Falk teaches that double bonds of the disubstituted 1,4-polybutadiene units are hydrogenated selectively in the presence of double bonds of the trisubstituted 1,4-polyisoprene units (which are not hydrogenated). We surprisingly discovered that the disubstituted double bonds of the 1,4-polybutadiene units are hydrogenated along with the monosubstituted double bonds of the 1,2-polybutadiene units, while the disubstituted double bonds of the 3,4-polyisoprene units are hydrogenated at a much slower rate than the aforementioned polybutadienes. Thus, in view of Falk's disclosure it is surprising that the disubstituted double bonds of the 1,4-polybutadiene units are hydrogenated selectively in the presence of the disubstituted double bonds of the 3,4-polyisoprene units. This is also surprising in view of the teachings of Hoxmeier, Published European Patent Application, Publication No. 0 315 280, who discloses that the disubstituted double bonds of the 1,4-polybutadiene units, monosubstituted double bonds of the 1,2-polybutadiene units and disubstituted double bonds of the 3,4-polyisoprene units are hydrogenated simultaneously at substantially the same rates. For example, for the block copolymers of this invention, wherein the I block is polyisoprene and the B block is polybutadiene, Fourier Transform Infrared (FTIR) analysis of selectively hydrogenated triblock polymers indicates that the hydrogenation of the double bonds of the 1,2-polybutadiene units proceeds most rapidly, followed by the hydrogenation of the double bonds of the 1,4-polybutadiene units. Infrared absorptions caused by these groups disappear prior to appreciable hydrogenation of the polyisoprene units.

After the I-B-I block copolymer is prepared, it is subjected to a selective hydrogenation reaction to hydrogenate primarily the B block of each of the triblocks. The selective hydrogenation reaction and the catalyst are described in detail below. After the hydrogenation reaction is completed, the selective hydrogenation catalyst is removed from the block copolymer, and the polymer is isolated by conventional procedures, e.g., alcohol flocculation, steam stripping of solvent or non-aqueous solvent evaporation. An antioxidant, e.g., Irganox 1076 (from Ciba-Geigy), is normally added to the polymer solution prior to polymer isolation.

The isolated polymer is vulcanizable through the α-ω unsaturated end blocks I by a number of well known processes utilized currently for thermosetting hydrocarbon elastomers. Such processes are detailed in RUBBER TECHNOLOGY, THIRD EDITION, VAN NOSTRAND REINHOLD COMPANY, New York, 1987, Maurice Morton, Editor, Chapters 2, 9 and 10, incorporated herein by reference.

Triblock Copolymer Of Poly-Diene Center Block And Terminal Blocks of Aryl-Substituted Olefin/Diene Copolymer In this alternative embodiment of the invention, the block copolymer comprises at least one triblock of:

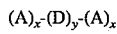

wherein the block A is a copolymer of about 30 to about 70%, preferably about 40 to about 60% by mole of at least one aryl-substituted olefin, and about 30 to about 70%, preferably about 40 to about 60%, by mole of at least one conjugated diene of formula (1), defined above. The block A is either a block or a random copolymer. The most preferred conjugated diene of formula (1) is isoprene. In this block copolymer, D is a block of a polymer of at least one conjugated diene of formula (3), discussed above, which is different from the conjugated diene of formula (1) used to polymerize the block A. In this block copolymer, x represents the total number of monomer units in the block A, such that the block copolymer comprises about 2 to about 30%, preferably about 4 to about 16% by wt. of the A blocks and y represents the total number of monomer units in the block D, such that the block copolymer comprises about 40 to about 96%, preferably about 68 to about 92% by wt. of the D blocks. The block copolymer of this embodiment may contain several blocks of the aforementioned formula, e.g., 5, so long as it is terminated at both ends with the block A, but, preferably, it contains only three blocks A-D-A. Suitable aryl-substituted olefins used to polymerize the block A have the formula

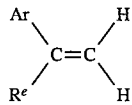

where Ar is phenyl, alkyl-substituted phenyl, naphthyl or alkyl-substituted naphthyl, and $R^e$ is hydrogen, methyl, ethyl, propyl, butyl or aryl. Examples of suitable aryl-substituted olefins are styrene, 2-phenyl alpha-olefins, such as alpha-methyl styrene, 1,1-diphenyl ethylene, alkylated styrenes, vinyl naphthalene, or any alkylated vinyl naphthalenes. Suitable alkyl substituents in the alkylated styrenes or alkylated vinyl naphthalenes are methyl, ethyl, propyl, sec-butyl and tert-butyl. Each of the alkylated styrenes or vinyl naphthalenes may contain one or more alkyl substituents. Preferred aryl-substituted olefins are styrene, vinylnaphthalene, alpha-methyl styrene, vinyltoluene and diphenylethylene. The microstructure of the polymerized diene of formula (1) is not critical, but can be controlled in the manner discussed above. The block copolymer of this embodiment is polymerized by any conventional block copolymerization process, such as anionic polymerization discussed in detail below.

The scope of this embodiment, and of any other embodiment of the invention wherein the block D is used, also encompasses polymers wherein the central (middle) block D may be comprised of copolymers of one or more conjugated diene of formula (3) and controlled amounts (about 0.3 to about 50 mole %) of an aryl-substituted olefin, e.g., styrene or other suitable monomers (such as alkylated styrene, vinyl napthalene or alkylated vinyl napthalene), incorporated for control of glass transition temperature (Tg), density, solubility parameters and refractive index.

The scope of this embodiment, and of any other embodiment of the invention using the block A, also encompasses polymers wherein the blocks A are prepared by, initially, polymerizing at least one aryl-substituted olefin alone, and subsequently reacting the resulting poly-aryl-substituted olefin with any compounds which, after chemical reaction with the poly-aryl-substituted olefin, will provide the residual double bonds on the A blocks, as defined above in conjunction with the discussion of the conjugated diene of formula (1). The resulting block A will therefore have substantially the same residual unsaturation (residual double bonds) on the terminal blocks A as any other block A made in accordance with this embodiment (or any other embodiment using the block A).

In the most preferred embodiment, the block A of this triblock copolymer is polymerized from isoprene and styrene in the molar proportion of about 1:1. Most preferably, in this embodiment of the invention, the A block is polymerized from isoprene and styrene, and the D block from 1,3-butadiene, in such proportions that the final copolymer comprises about 1.5 to about 6% wt. of the isoprene, about 2.5 to about 10% wt. of the styrene, and about 84 to about 96% wt. of the butadiene units.

After the polymerization is completed, the block copolymer is subjected to a selective hydrogenation reaction. After selective hydrogenation, the polymer contains a sufficient amount of its original unsaturation in the terminal blocks A to cure the block polymer, thereby permitting chemical crosslinking or functionalization in the manner discussed below, while the middle block D contains substantially none of the original unsaturation. For example, for a block copolymer wherein the A blocks are copolymers of styrene and isoprene and the D block is polybutadiene, the Iodine Number before selective hydrogenation for each of the A blocks is 120–180 and for the D block it is 470. After selective hydrogenation, the Iodine Number for each of the A blocks is about 20 to about 180 and for the D block it is about 0 to about 10, and preferably about 0 to about 2.5. Generally, for a block copolymer wherein the A and D blocks are polymerized from any of the monomers suitable for their polymerization, discussed above, the Iodine Number for the A blocks after the selective hydrogenation is completed is about 20 to about 100%, preferably about 100% of the Iodine Number prior to the selective hydrogenation reaction, and for the D blocks it is about 0 to about 10%, preferably about 0 to about 0.5%, and most preferably about 0% of the Iodine Number prior to the selective hydrogenation reaction. Thus, in this embodiment, the block D is also selectively hydrogenated in the same manner as discussed above for the central block B of the first embodiment of the invention.

The block copolymer of this embodiment is also a liquid, and, after selective hydrogenation, the unsaturated groups in the terminal A blocks of each of the triblocks provide a means of crosslinking the copolymer or functionalizing the terminal blocks A, in the manner discussed elsewhere in this application.

Triblock Copolymer of at Least One Poly-Diene Center Block, and at Least One Terminal Block of Aryl-Substituted Olefin/Diene Copolymer In this embodiment of the invention, the block copolymer comprises at least one triblock of:

I-D-A where the block I is a polymer of at least one polymerized diene of formula (1), defined above, the block D is a polymer of at least one conjugated diene of formula (3), defined above, which is different from the conjugated diene of formula (1), and the block A is a copolymer of at least one aryl-substituted olefin and at least one conjugated diene of formula (1), both defined above. The block A is a copolymer of about 30 to about 70%, preferably about 40 to about 60% by mole of at least one aryl-substituted olefin, and about 30 to about 70%, preferably about 40 to about 60% by mole of at least one conjugated diene of formula (1), preferably isoprene. This block copolymer comprises about 1 to about 15, preferably about 2 to about 8% wt. of the blocks I, about 2 to about 30, preferably about 4 to about 16% wt. of the blocks A, and about 55 to about 97, preferably about 76 to about 94% wt. of the blocks D. The block of this embodiment may also contain several, e.g. 5–7, blocks of the aforementioned formulae so long as it is terminated at both ends thereof with blocks I or A. The block copolymer is polymerized by any conventional block copolymerization process, such as anionic polymerization, discussed in detail below.

The scope of this embodiment of the invention also encompasses polymers wherein the central block D may be comprised of copolymers of one or more conjugated diene of formula (3) and controlled amounts (about 0.3 to about 30 mole %) of an aryl-substituted olefin, e.g., styrene or other suitable monomers (such as alkylated styrene, vinyl napthalene or alkylated vinyl napthalene), incorporated for control of glass transition temperature ($T_g$), density, solubility parameters and refractive index. Suitable aryl-substituted olefins are those described below in conjunction with the second embodiment of the invention. Similarly, the scope of this embodiment also encompasses polymers wherein the central block D may be comprised of copolymers of one or more conjugated diene of formula (3) and any other anionically polymerizable monomer capable of polymerizing with the conjugated diene of formula (3).

This embodiment also encompasses polymers wherein the blocks A are prepared by, initially, polymerizing at least one aryl-substituted olefin alone, and, subsequently, reacting the resulting poly-aryl-substituted olefin with any compounds which, after chemical reaction with the poly-aryl-substituted olefin, will provide the residual double bonds to the A blocks, as defined above in conjunction with the discussion of the conjugated diene of formula (1). The resulting block A will therefore have substantially the same residual unsaturation (residual double bonds) on the terminal blocks A as any other block A made in accordance with this embodiment.

After the polymerization is completed the block copolymer is subjected to a selective hydrogenation reaction. After selective hydrogenation, the polymer contains a sufficient amount of its original unsaturation in the terminal blocks I and A to cure the block copolymer, thereby permitting chemical crosslinking or functionalization in the manner discussed below, while the middle block D contains substantially none of the original unsaturation. Generally, for a block copolymer wherein the I, D and A blocks are polymerized from any of the monomers suitable for their polymerization, discussed above, the Iodine Number for the I and A blocks after the selective hydrogenation is completed is about 10 to about 100%, preferably about 100% of the Iodine Number prior to the selective hydrogenation reaction, and for the D blocks it is about 0 to about 10%, preferably about 0 to about 0.5%, and most preferably 0% of the Iodine Number prior to the selective hydrogenation reaction. Thus, in this embodiment, the block D is also selectively hydrogenated in the same manner as discussed while the terminal blocks I and A retain a substantial amount of their original unsaturation.

The block copolymer of this embodiment is also a liquid, and, after selective hydrogenation, the unsaturated groups in the terminal blocks I and A of each of the triblocks provide a means of crosslinking the copolymer or functionalizing the terminal blocks I and A, in the manner discussed elsewhere in this application.

Random Copolymers

Random copolymers of this invention have controlled amounts of unsaturation incorporated randomly in an otherwise saturated backbone. In contrast to EPDM, the level of unsaturation can be inexpensively and easily controlled, e.g., to produce polymers having Iodine Number of about 5 to about 100, to provide a wide variation in vulcanization rate and potential co-curability with various highly unsaturated rubbers based on butadiene or isoprene.

In one embodiment, the random copolymers are polymerized from the same monomers used to polymerize the block copolymers $(I)_x$-$(B)_y$-$(I)_x$, i.e., from at least one conjugated diene of formula (1) and at least one conjugated diene of formula (3), both defined above, provided that the diene of formula (1) is different from the diene of formula (3). This random copolymer contains about 1.0 to about 25%, preferably about 1.0 to about 10% by mole of the polymerized conjugated diene of formula (1) and about 75 to about 99%, preferably about 90 to about 99% by mole of the polymerized conjugated diene of formula (3). Suitable conjugated dienes of formula (1) are exemplified above. The most preferred conjugated diene of formula (1) for the copolymerization of these random copolymers is isoprene. Suitable conjugated dienes of formula (3) are also exemplified above. 1, 3-butadiene is the most preferred conjugated diene of formula (3) for the polymerization of the random copolymer of this embodiment. Thus, most preferably, in this embodiment, the random copolymer is polymerized from isoprene and 1,3-butadiene, and it contains about 1 to about 20% wt. of the isoprene units and about 80 to about 99% wt. of the butadiene units. The isoprene units have primarily (i.e., about 50 to about 90% wt.) the 3, 4-microstructure.

In another embodiment, the random copolymers are polymerized from the same monomers used to polymerize the block copolymers $(A)_x$-$(C)_y$-$(A)_x$, i.e., from at least one aryl-substituted olefin, at least one conjugated diene of formula (1), and at least one conjugated diene of formula (3), providing that the conjugated diene of formula (1) is different from the conjugated diene of formula (3) used in the polymerization. The conjugated dienes of formulae (1) and (3) are defined above and the aryl-substituted olefins are also the same as those defined above. This alternative random copolymer contains about 0.3 to about 15% by mole of the aryl-substituted olefin, about 1.0 to about 25%, preferably about 1.0 to about 10%, by mole of the conjugated diene of formula (1) the remainder being the conjugated diene of formula (3).

The random copolymers are subjected to the selective hydrogenation reaction discussed above for the block copolymers, during which polymerized conjugated diene units of formula (3) are substantially completely hydrogenated, while the polymerized conjugated diene units of formula (1) are hydrogenated to a substantially lesser extent, i.e., to such an exent that they retain a sufficient amount of their original unsaturation to vulcanize the copolymer, thereby producing liquid elastomers having random unsaturation proportional to the unsaturation in the polymerized dienes of formula (1) For example, for a random copolymer polymerized from a diene of formula (1) and a different diene of formula (3), the Iodine Number before selective hydrogenation for the polymer is about 450. After selective hydrogenation, the Iodine Number for the polymer is about 10 to about 50, with most of the unsaturation being contributed by the diene of formula (1).

Similarly, for a random copolymer of aryl-substituted olefins, a conjugated diene of formula (1) and a conjugated diene of formula (3), different from the conjugated diene of formula (1), the Iodine Number before selective hydrogenation for the polymer is about 250 to about 450. After selective hydrogenation, the Iodine Number for the polymer is about 10 to about 100, most of it being contributed by the diene of formula (1).

The hydrogenated polymers may be vulcanized. The vulcanized random copolymers of this invention have elastomeric properties similar to those of EPDM. The vulcanization rate of the polymers can be easily and inexpensively increased by increasing the content of the diene of formula (1), i.e., isoprene in the most preferred embodiment, in either embodiment of the random copolymers to from about 5 to about 20% by mole.

Star-Branched Polymers

The invention is also directed to star-branched block and random polymers.

The star-branched block polymers are made from any combination of blocks I and B, A and D, or I, D and A all defined above, providing that each free end (i.e., the uncoupled end) of the star-branched polymer is either an I or an A block in the star-branched block polymers made from blocks I and B, A and D or I, D and A, respectively. The star-branched I-B block polymers comprise about 0.5 to about 25%, preferably about 1 to about 5% by wt. of the I blocks, and about 75 to about 99.5%, preferably about 95 to about 99% by wt. of the B blocks. The star-branched A-D block polymers comprise about 4 to about 60%, preferably about 8 to about 32% by wt. of the A blocks, and about 40 to about 96%, preferably about 68 to about 92% by wt. of the D blocks. The star-branched I-D-A block polymers comprise about 1 to about 15, preferably about 2 to about 8% wt. of the blocks I, about 2 to about 30, preferably about 4 to about 16% wt. of the blocks A and about 55 to about 97, preferably about 76 to about 94% wt. of the blocks D. The block A of this copolymer is either a block or a random copolymer of about 30 to about 70% by mole of at least one aryl-substituted olefin and about 30 to about 70% by mole of at least one conjugated diene of formula (1).

The star-branched block polymers are selectively hydrogenated in the selective hydrogenation process of this invention to such an extent that blocks B or D contain substantially none of the original unsaturation, while each of the blocks I and A, respectively, retains a sufficient amount of the original unsaturation of the conjugated dienes present in these blocks to cure the star-branched block polymers. Thus, for the I-B star-branched block polymer, after the selective hydrogenation reaction, the Iodine Number for the I blocks is about 10 to about 100%, preferably about 25 to about 100%, more preferably about 50 to about 100%, and most preferably about 100% of the Iodine Number prior to the selective hydrogenation reaction, and for the B blocks it is about 0 to about 10%, preferably about 0 to about 0.5% of the Iodine Number prior to the selective hydrogenation reaction. Similarly, for the A-D star-branched block polymer, after the selective hydrogenation reaction, the Iodine Number for the A blocks is about 10 to about 100%, preferably about 25 to about 100%, more preferably about 50 to about 100%, and most preferably about 100% of the Iodine Number prior to the selective hydrogenation reaction, and for the D blocks it is about 0 to about 10%, preferably about 0 to about 0.5% of the Iodine Number prior to the selective hydrogenation reaction. Similarly, for the I-D-A star-branched block polymer, the Iodine Number for each of the I and A blocks after the selective hydrogenation is completed is about 10 to about 100%, preferably about 100% of the Iodine Number prior to the selective hydrogenation reaction, and for the D blocks it is about 0 to about 10%, preferably about 0 to about 0.5%, and most preferably 0% of the Iodine Number prior to the selective hydrogenation reaction. Thus, in this embodiment, the block D is also selectively hydrogenated in the same manner as discussed above for the central blocks B and D of the other embodiments of the invention.

The star-branched random polymers are made from any combination of at least one diene of formula (1) and at least one diene of formula (3), different from the diene of formula (1), or from any combination of at least one aryl-substituted olefin, at least one diene of formula (1) and at least one diene of formula (3), different from the diene of formula (1), all of which are the same as those discussed above. The star-branched random polymers of the dienes of formulae (1) and (3), which must be different from each other, comprise about 1 to about 25%, preferably about 1 to about 10% by wt. of the diene of formula (1) and about 75 to about 99%, preferably about 90 to about 99% by wt. the diene of formula (3). The star-branched random polymers of the aryl-substituted olefin and the dienes of formulae (1) and (3) comprise about 0.3 to about 15% by mole of the aryl-substituted olefin, about 1 to about 25%, preferably about 1 to about 10% by mole of the conjugated diene of formula (1), and the remainder of the conjugated diene of formula (3). The star-branched random polymers are also selectively hydrogenated in the selective hydrogenation process of this invention to such an extent that the polymerized dienes of formula (3) contain substantially none of the original unsaturation, while the polymerized dienes of formula (1) retain a sufficient amount of the original unsaturation to cure the star-branched random polymers. Thus, for the star-branched random polymer of the conjugated diene of formula (1) and a different diene of formula (3), both identified above, the Iodine Number for the polymerized diene of formula (1), after the selective hydrogenation reaction, is about 10 to about 100%, preferably about 25 to about 100%, more preferably about 50 to about 100%, and most preferably about 100% of the Iodine Number prior to the selective hydrogenation reaction, and for the polymerized diene of formula (3) it is about 0 to about 10%, preferably about 0 to about 0.5% of the Iodine Number prior to the selective hydrogenation reaction. Similarly, for the star-branched random polymers made from at least one aryl-substituted olefin, at least one diene of formula (1) and at least one diene of formula (3), the Iodine Number for the polymerized diene of formula (1), after the selective hydrogenation reaction, is about 10 to about 100%, preferably about 25 to about 100%, more preferably about 50 to about 100%, and most preferably about 100% of the Iodine Number prior to the selective hydrogenation reaction, and for the polymerized diene of formula (3) it is about 0 to about 10%, preferably about 0 to about 0.5% of the Iodine Number prior to the selective hydrogenation reaction.

Blends Of Inventive Polymers With Other Materials

The block and random copolymers of this invention can, of course, be blended with any unsaturated elastomers, in which case the degree of unsaturation of the copolymers of the invention can be adjusted so that the vulcanization rate of the two materials is substantially the same. Suitable elastomers which can be blended with the copolymers of this invention are liquid butyl, liquid polyisoprene, liquid polybutadiene (modified and unmodified), and liquid EPDM. Suitable solid rubbers with which the copolymers of this invention can be blended are, e.g., SBR, polyisoprene, polybutadiene, EPDM, butyl rubber and neoprene.

The block and random copolymers of this invention can, of course, be compounded with ingredients known to those skilled in the art, e.g., fillers, such as silica, carbon black, extender oils, antioxidants, tackifying agents, vulcanizing agents and similar materials.

Polymerization Reaction

The block copolymers of this invention are polymerized by any known block polymerization processes, preferably by an anionic polymerization process. Anionic polymerization is well known in the art and it is utilized in the production of a variety of commercial polymers. An excellent comprehensive review of the anionic polymerization processes appears in the text ADVANCES IN POLYMER SCIENCE 56, ANIONIC POLYMERIZATION, pp. 1–90, Springer-Verlag, Berlin, Heideberg, New York, Tokyo 1984 in a monograph entitled ANIONIC POLYMERIZATION OF NON-POLAR MONOMERS INVOLVING LITHIUM, by R. N. Young, R. P. Quirk and L. J. Fetters, incorporated herein by reference. The anionic polymerization process is conducted in the presence of a suitable anionic catalyst (also known as an initiator), such as n-butyl-lithium, sec-butyl-lithium, t-butyl-lithium, sodium naphthalide or cumyl potassium. The amount of the catalyst and the amount of the monomer in the polymerization reaction dictate the molecular weight of the polymer. The polymerization reaction is conducted in solution using an inert solvent as the polymerization medium, e.g., aliphatic hydrocarbons, such as hexane, cyclohexane or heptane, or aromatic solvents, such as benzene or toluene. In certain instances, inert polar solvents, such as tetrahydrofuran, can be used alone as a solvent, or in a mixture with a hydrocarbon solvent.

The block polymerization process will be exemplified below for the polymerization of the first embodiment of the invention, and specifically for the preferred embodiment thereof, i.e., a triblock of polyisoprene-polybutadiene-polyisoprene. However, it will be apparent to those skilled in the art that the same process principles can be used for the polymerization of all copolymers of the invention.

The process, when using a lithium-based catalyst, comprises forming a solution of the isoprene monomer in an inert hydrocarbon solvent, such as cyclohexane, modified by the presence therein of one or more polar compounds selected from the group consisting of ethers, thioethers and tertiary amines, e.g., tetrahydrofuran. The polar compounds are necessary to control the microstructure of the butadiene center block, i.e., the content of the 1,2-structure thereof. The higher the content of the polar compounds, the higher will be the content of the 1,2-structure in these blocks. Since the presence of the polar compound is not essential in the formation of the first polymer block with many initiators unless a high 3,4-structure content of the first block is desired, it is not necessary to introduce the polar compound at this stage, since it may be introduced just prior to or together with the addition of the butadiene in the second polymerization stage. Examples of polar compounds which may be used are dimethyl ether, diethyl ether, ethyl methyl ether, ethyl propyl ether, dioxane, diphenyl ether, tripropyl amine, tributyl amine, trimethyl amine, triethyl amine, and N-,N-,N'-,N'-tetramethyl ethylene diamine. Mixtures of the polar compounds may also be used. The amount of the polar compound depends on the type of the polar compound and the polymerization conditions as will be apparent to those skilled in the art. The effect of polar compounds on the polybutadiene microstructure is detailed in ANTKOWIAK et al, TEMPERATURE AND CONCENTRATION EFFECTS ON POLAR-MODIFIED ALKYL LITHIUM POLYMERIZATIONS AND COPOLYMERIZATIONS, JOURNAL OF POLYMER SCIENCE: Part A-1, Vol. 10, 1319–1334 (1972), incorporated herein by reference. The polar compounds also accelerate the rate of polymerization. If monomers other than 1,3-butadiene, e.g., pentadiene, are used to polymerize the central blocks B or D, polar compounds are not necessary to control the microstructure because such monomers will inherently produce polymers which do not possess crystallinity after hydrogenation.

When the alkyl lithium-based initiator, a polar compound and an isoprene monomer are combined in an inert solvent, polymerization of the isoprene proceeds to produce the first terminal block whose molecular weight is determined by the ratio of the isoprene to the initiator. The "living" polyisoprenyl anion formed in this first step is utilized as the catalyst for further polymerization. At this time, butadiene monomer is introduced into the system and block polymerization of the second block proceeds, the presence of the polar compound now influencing the desired degree of branching (1,2-structure) in the polybutadiene block. The resulting product is a living diblock polymer having a terminal anion and a lithium counterion. The living diblock polymer serves as a catalyst for the growth of the final isoprene block, formed when isoprene monomer is again added to the reaction vessel to produce the final polymer block, resulting in the formation of the I-B-I triblock. Upon completion of polymerization, the living anion, now present at the terminus of the triblock, is destroyed by the addition of a proton donor, such as methyl alcohol or acetic acid. The polymerization reaction is usually conducted at a temperature of between 0° C. and about 100° C., although higher temperatures can be used. Control of a chosen reaction temperature is desirable since it can influence the effectiveness of the polar compound additive in controlling the polymer microstructure. The reaction temperature can be, for example, from 50° to 80° C. The reaction pressure is not critical and varies from atmospheric to about 100 psig.

If the polar compounds are utilized prior to the polymerization of the first I segment, I blocks with high 3,4-unit content are formed. If polar compounds (some of which can be Lewis bases) are added after the initial I segment is prepared, the first I segment will possess a high percentage of 1,4-microstructure (which is trisubstituted), and the second I segment will have a high percentage of 3,4-microstructure.

The production of triblock polymers having a high 1,4-unit content on both of the terminal I blocks is also possible by the use of coupling techniques illustrated below for a polyisoprene-polybutadiene-polyisoprene block copolymer:

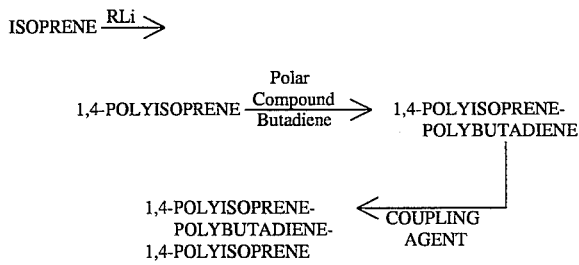

The substitution of myrcene for the isoprene during the polymerization of the I blocks insures the incorporation of a high proportion of trisubstituted double bonds, even in the presence of polar compounds since myrcene contains a pendant trisubstituted double bond which is not involved in the polymerization process. In a coupling process, similar to that described above, block polymers containing polyisoprene end blocks (or any other polymerized monomer suitable for use in the I block) having a high 3,4-microstructure content can be obtained by adding the polar compound prior to the isoprene (or another monomer) polymerization.

The use of the coupling technique for the production of triblock polymers reduces the reaction time necessary for the completion of polymerization, as compared to sequential addition of isoprene, followed by butadiene, followed by isoprene. Such coupling techniques are well known and utilize coupling agents, such as esters, $CO_2$, iodine, dihaloalkanes, silicon tetrachloride, divinyl benzene, alkyl trichlorosilanes and dialkyl dichlorosilanes. The use of tri- or tetra-functional coupling agents, such as alkyl trichlorosilanes or silicon tetrachloride, permits the formation of macromolecules having 1- or 2- main chain branches, respectively. The addition of divinyl benzene as a coupling agent has been documented to produce molecules having up to 20 or more separately joined segments.

The use of some of the coupling agents provides a convenient means of producing star-branched block and random polymers. The star-branched block polymers are made from any combination of blocks I and B, A and D or I, D and A, defined above, providing that each free end (i.e., the uncoupled end) of the star-branched polymer is either an I or an A block, respectively. The star-branched random polymers are made from any combination of at least one diene of formula (1) and at least one diene of formula (3), different from the diene of formula (1), or from at least one aryl-substituted olefin, at least one diene of formula (1) and at least one diene of formula (3), different from the diene of formula (1). The molecular weight of the star-branched block and random copolymers will depend on the number of branches in each such copolymer, as will be apparent to those skilled in the art. Suitable coupling agents and reactions are disclosed in the following references which are incorporated herein by reference: U.S. Pat. Nos. 3,949,020; 3,594,452; 3,598,887; 3,465,065; 3,078,254; 3,766,301; 3,632,682; 3,668,279; and Great Britain patents 1,014,999; 1,074,276; 1,121,978.

The random copolymers of the invention are polymerized and/or coupled in a similar fashion, but all monomers, e.g., isoprene and butadiene, are mixed in a proper ratio prior to the reaction with the polar compound-modified alkyllithium. In the random polymer preparation, of course, only one stage is necessary.

Selective Hydrogenation

The selective hydrogenation reaction will also be described below using a triblock of polyisoprene-polybutadiene-polyisoprene as an example. However, it will be apparent to those skilled in the art that any polymers of this invention can be selectively hydrogenated in the same manner.

The block copolymer is selectively hydrogenated to saturate the middle (polybutadiene) block of each of the triblocks. The method of selectively hydrogenating the polybutadiene block is similar to that of Falk, "Coordination Catalysts For The Selective Hydrogenation of Polymeric Unsaturation", JOURNAL OF POLYMER SCIENCE: PART A-1, Volume 9, 2617–2623 (1971), but it is conducted with a novel hydrogenation catalyst and process used herein. Any other known selective hydrogenation methods may also be used, as will be apparent to those skilled in the art, but it is preferred to use the method described herein. In summary, the selective hydrogenation method preferably used herein comprises contacting the previously-prepared block copolymer with hydrogen in the presence of the novel catalyst composition.

The novel hydrogenation catalyst composition and hydrogenation process are described in detail in application, Ser. No. 07/466,136 filed on Jan. 16, 1990. The hydrogenation catalyst composition is synthesized from at least one transition metal compound and an organometallic reducing agent. Suitable transition metal compounds are compounds of metals of Group IVb, Vb, VIb or VIII, preferably IVb or VIII of the Periodic Table of the Elements, published in LANGE'S HANDBOOK OF CHEMISTRY (13th Edition, 1985) McGraw-Hill Book Company, New York (John A. Dean, editor). Non-limiting examples of such compounds are metal halides, e.g., titanium tetrachloride, vanadium tetrachloride; vanadium oxytrichloride, titanium and vanadium alkoxides, wherein the alkoxide moiety has a branched or unbranched alkyl radical of 1 to about 20 carbon atoms, preferably 1 to about 6 carbon atoms. Preferred transition metal compounds are metal carboxylates or alkoxides of Group IVb or VIII of the Periodic Table of the Elements, such as nickel (II) 2-ethylhexanoate, titanium isopropoxide, cobalt (II) octoate, nickel (II) phenoxide and ferric acetylacetonate.

The organometallic reducing agent is any one or a combination of any of the materials commonly employed to activate Ziegler-Natta olefin polymerization catalyst components containing at least one compound of the elements of Groups Ia, IIa, IIb, IIIa, or IVa of the Periodic Table of the Elements. Examples of such reducing agents are metal alkyls, metal hydrides, alkyl metal hydrides, alkyl metal halides, and alkyl metal alkoxides, such as alkyllithium compounds, dialkylzinc compounds, trialkylboron compounds, trialkylaluminum compounds, alkylaluminum halides and hydrides, and tetraalkylgermanium compounds. Mixtures of the reducing agents may also be employed. Specific examples of useful reducing agents include n-butyllithium, diethylzinc, di-n-propylzinc, triethylboron, diethylaluminumethoxide, triethylaluminum, trimethylaluminum, triisoutylaluminum, tri-n-hexylaluminum, ethylaluminum dichloride, dibromide, and dihydride, isobutyl aluminum dichloride, dibromide, and dihyride, diethylaluminum chloride, bromide, and hydride, di-n-propylaluminum chloride, bromide, and hydride diisobutylaluminum chloride, bromide and hydride, tetramethylgermanium, and tetraethylgermanium. Organometallic reducing agents which are preferred are Group IIIa metal alkyls and dialkyl metal halides having 1 to about 20 carbon atoms per alkyl radical. More preferably, the reducing agent is a trialkylaluminum compound having 1 to about 6 carbon atoms per alkyl radical. Other reducing agents which can be used herein are disclosed in Stevens et al, U.S. Pat. No. 3,787,384, column 4, line 45 to column 5, line 12 and in Strobel et al, U.S. Pat. No. 4,148,754, column 4, line 56 to column 5, line 59, the entire contents of both of which are incorporated herein by reference. Particularly preferred reducing agents are metal alkyl or hydride derivatives of a metal selected from Groups Ia, IIa and IIIa of the Periodic Table of the Elements, such as n-butyl lithium, sec-butyl lithium, n-hexyl lithium, phenyl-lithium, triethylaluminum, tri-isobutylaluminum, trimethylaluminum, diethylaluminum hydride and dibutylmagnesium.

The molar ratio of the metal derived from the reducing agent to the metal derived from the transition metal compound will vary for the selected combinations of the reducing agent and the transition metal compound, but in general it is about 1:1 to about 12:1, preferably about 1.5:1 to about 8:1, more preferably about 2:1 to about 7:1 and most preferably about 2.5:1 to about 6:1. It will be apparent to those skilled in the art that the optimal ratios will vary depending upon the transition metal and the organometallic agent used, e.g., for the trialkylaluminum/nickel(II) systems, the preferred aluminum: nickel molar ratio is about 2.5:1 to about 4:1, for the trialkylaluminum/cobalt(II) systems, the preferred aluminum: cobalt molar ratio is about 3:1 to about 4:1 and for the trialkylaluminum/titanium(IV) alkoxides systems, the preferred aluminum:titanium molar ratio is about 3:1 to about 6:1.

The mode of addition and the ratio of the reducing agent to the transition metal compound are important in the production of the novel hydrogenation catalyst having superior selectivity, efficiency and stability, as compared to prior art catalytic systems. During the synthesis of the catalysts it is preferred to maintain the molar ratio of the reactants used to synthesize the catalyst substantially constant. This can be done either by the addition of the reducing agent, as rapidly as possible, to a solution of the transition metal compound, or by a substantially simultaneous addition of the separate streams of the reducing agent and the transition metal compound to a catalyst synthesis vessel in such a manner that the selected molar ratios of the metal of the reducing agent to the metal of the transition metal compound are maintained substantially constant throughout substantially the entire time of addition of the two compounds. The time required for the addition must be such that excessive pressure and heat build up are avoided, i.e., the temperature should not exceed about 80° C. and the pressure should not exceed the safe pressure limit of the catalyst synthesis vessel.

In a preferred embodiment, the reducing agent and the transition metal compound are added substantially simultaneously to the catalyst synthesis vessel in such a manner that the selected molar ratio of the reducing agent to the transition metal compound is maintained substantially constant during substantially the entire time of the addition of the two compounds. This preferred embodiment permits the control of the exothermic reaction so that the heat build up is not excessive, and the rate of gas production during the catalyst synthesis is also not excessive-accordingly the gas build-up is relatively slow. In this embodiment, carried out with or without a solvent diluent, the rate of addition of the catalyst components is adjusted to maintain the synthesis reaction temperature at or below about 80° C., which promotes the formation of the selective hydrogenation catalyst. Furthermore, the selected molar ratios of the metal of the reducing agent to the metal of the transition metal compound are maintained substantially constant throughout the entire duration of the catalyst preparation when the simultaneous mixing technique of this embodiment is employed.

In another embodiment, the catalyst is formed by the addition of the reducing agent to the transition metal compound. In this embodiment, the timing and the order of addition of the two reactants is important to obtain the hydrogenation catalyst having superior selectivity, efficiency and stability. Thus, in this embodiment, it is important to add the reducing agent to the transition metal compound in that order in as short a time period as practically possible. In this embodiment, the time allotted for the addition of the reducing agent to the transition metal compound is critical for the production of the novel catalyst. The term "as short a time period as practically possible" means that the time of addition is as rapid as possible, such that the reaction temperature is not higher than about 80° C. and the reaction pressure does not exceed the safe pressure limit of the catalyst synthesis vessel. As will be apparent to those skilled in the art, that time will vary for each synthesis and will depend on such factors as the types of the reducing agents, the transition metal compounds and the solvents used in the synthesis, as well as the relative amounts thereof, and the type of the catalyst synthesis vessel used. For purposes of illustration, a solution of about 15 ml of triethylaluminum in hexane should be added to a solution of nickel(II) octoate in mineral spirits in about 10–30 seconds. Generally, the addition of the reducing agent to the transition metal compound should be carried out in about 5 seconds (sec) to about 5 minutes, depending on the quantities of the reagents used. If the time period during which the reducing agent is added to the transition metal compound is prolonged, e.g., more than 15 minutes, the synthesized catalyst is less selective, less stable and may be heterogeneous.

In the embodiment wherein the reducing agent is added as rapidly as possible to the transition metal compound, it is also important to add the reducing agent to the transition metal compound in the aforementioned sequence to obtain the novel catalyst. The reversal of the addition sequence, i.e., the addition of the transition metal compound to the reducing agent, or the respective solutions thereof, is detrimental to the stability, selectivity, activity and homogeneity of the catalyst and is therefore undesirable.

In all embodiments of the hydrogenation catalyst synthesis, it is preferred to use solutions of the reducing agent and the transition metal compound in suitable solvents, such as hydrocarbon solvents, e.g., cyclohexane, hexane, pentane, heptane, benzene, toluene or mineral oils. The solvents used to prepare the solutions of the reducing agent and of the transition metal compound may be the same or different, but if they are different, they must be compatible with each other so that the solutions of the reducing agent and the transition metal compound are fully soluble in each other.

The hydrogenation process comprises contacting the unsaturated polymer to be hydrogenated with an amount of the catalyst solution containing about 0.1 to about 0.5, preferably about 0.2 to about 0.3 mole percent of the transition metal based on moles of the polymer unsaturation.

The hydrogen partial pressure is about 5 psi to about several hundred psi, but preferably it is about 10 to about 100 psi. The temperature of the hydrogenation reaction mixture is about 25 to about 80° C., since higher temperatures may lead to catalyst deactivation. The length of the hydrogenation reaction may be as short as 30 minutes and, as will be apparent to those skilled in the art, depends to a great extent on the actual reaction conditions employed. The hydrogenation process may be monitored by any conventional means, e.g., infra-red spectroscopy, hydrogen flow rate, total hydrogen consumption, or any combination thereof.

Upon completion of the hydrogenation process, unreacted hydrogen is either vented or consumed by the introduction of the appropriate amount of an unsaturated material, such as 1-hexene, which is converted to an inert hydrocarbon, e.g., hexane. Subsequently, the catalyst is removed from the resulting polymer solution by any suitable means, selected depending on the particular process and polymer. For a low molecular weight material, for example, catalyst residue removal may consist of a treatment of the solution with an oxidant, such as air, and subsequent treatment with ammonia and optionally methanol in amounts equal to the molar amount of the metals (i.e., the sum of the transition metal and the metal of the reducing agent) present in the hydrogenation catalyst to yield the catalyst residues as a filterable precipitate, which is filtered off. The solvent may then be removed by any conventional methods, such as vacuum stripping, to yield the product polymer as a clear, colorless fluid.

Alternatively, and in a preferred embodiment, upon completion of the hydrogenation reaction, the mixture is treated with ammonia in the molar amount about equal to that of the metals (i.e., the sum of the transition metal and the metal of the reducing agent) and aqueous hydrogen peroxide, in the molar amount equal to about one half to about one, preferably one half, of the amount of the metals. Other levels of the ammonia and peroxide are also operative, but those specified above are particularly preferred. In this method, a precipitate forms, which may be filtered off as described above.

In yet another alternative method, the catalyst may be removed by extraction with an aqueous mineral acid, such as sulfuric, phosphoric or hydrochloric acid, followed by washing with distilled water. A small amount of a material commonly used as an aid in removing transition metal-based catalysts, such as a commercially available high molecular weight diamine, e.g., Jeffamine D-2000 from Texaco, may be added to aid in phase separation and catalyst removal during the extractions. The resultant polymer solution is then dried over a drying agent, such as magnesium sulfate, separated from the drying agent and the solvent is then separated by any conventional methods, such as vacuum stripping, to yield a polymer as a clear fluid. Other methods of polymer isolation, such as steam or alcohol flocculation, may be employed depending upon the hydrogenated polymer properties.

Crosslinking And Functionalization Of The Terminal Blocks

In addition to acting as sites for vulcanization, the unsaturated terminal blocks of the block polymers of this invention can be chemically modified to provide benefits obtained with similar modifications of existing commercial materials, such as butyl rubber or EPDM. In some instances, the benefits obtained by a chemical modification of butyl rubber or EPDM may be magnified using the elastomers of our invention as a matrix instead of the butyl rubber or EPDM of similar molecular weight because of their intrinsically superior elastomeric properties.

It is known that the halogenation of the unsaturation in butyl rubber (based upon isoprene monomer) prior to the vulcanization treatment, produces dramatic changes in vulcanization rate and provides greater versatility in the choice of vulcanizing agents. Since the residual unsaturated groups in the first embodiment of our invention, present in the I block, in the most preferred embodiment, are also based on isoprene monomer, the halogenation of the polymer of this embodiment provides the same benefits, but with the retention of the greater elongation characteristics inherent in the invention polymer. The same benefits will be obtained with any other dienes which can be used to prepare the block I of this embodiment of the invention, and therefore any polymers of this invention containing any such dienes can be halogenated in the same manner as the butyl rubber. Any other polymers of this invention containing the polymerized dienes of formula (1) or blocks I can also be halogenated in the same manner.

It is also known that the reaction of EPDM with maleic anhydride at elevated temperatures (e.g., about 150° C. to about 250° C.) produces maleic modified EPDM which is used commercially as an impact modifier, particularly for Nylon. Similar modification of the polymers of any embodiments of our invention occurs readily, since the residual isoprene unsaturation, primarily of the 3,4-type, illustrated above, is known to be more reactive with maleic anhydride than are the internal bonds found in EPDM. The resultant product provides improved impact properties when blended with Nylon.

The above examples illustrate only some of the potentially valuable chemical modifications of the polymers of this invention. The liquid polymers of this invention provide a means for a wide variety of chemical modifications only at the ends of the molecule (i.e., at the I blocks only), thereby presenting the opportunity to prepare materials previously impossible because of the lack of availability of such polymers. Some examples of well known chemical reactions which can be performed on polymers of this invention are found in E. M.FETTES, CHEMICAL REACTIONS OF POLYMERS, High Polymers, Vol. 19, John Wiley, New York, 1964, incorporated herein by reference.

Until the instant invention, it has not been possible to produce liquid hydrocarbon elastomers having the capability of maintaining a large distance between crosslinks (high $M_c$) after vulcanization. Our invention provides block hydrocarbon polymers capable of being vulcanized to a perfect network with a distance between crosslinks substantially equivalent to the dimensions of the unvulcanized elastomeric molecule. In addition to the expected improvements in elastomeric properties, the saturated main chain of the polymers of our invention provides a high degree of oxidative and thermal stability. Unique materials can also be obtained by chemical modifications of the block polymers of this invention, since such modifications can be carried out selectively only at the unsaturated terminal ends of the molecules.

The crosslinking of the selectively hydrogenated block polymers of this invention is conducted in a conventional manner by contacting the block copolymer with a suitable crosslinking agent or a combination of such agents. The crosslinking process produces a copolymer having uniform distance between cross-links.

The block copolymers can also be functionalized by reacting the terminal blocks containing unsaturated groups with various reagents to produce functional groups, such as hydroxyl, epoxy, sulfonic acid, mercapto, acrylate or carboxyl groups. Functionalization methods are well known in the art. The functional groups can be used to produce both covalent and ionic crosslinks.

The random copolymers may also be cross-linked or functionalized in the same manner as the block copolymers.

The following Examples illustrate additional features of the invention. However, it will be apparent to those skilled in the art that the specific reactants and reaction conditions used in the Examples do not limit the scope of the invention.

In all of the following examples, the experimental work was performed with dried reactors and equipment and under strictly anaerobic conditions. Extreme care must be used to exclude air, moisture and other impurities capable of interfering with the delicate chemical balance involved in the synthesis of the polymers of this invention, as will be apparent to those skilled in the art.

EXAMPLE I (Isoprene-Butadiene-Isoprene Triblock Polymer)

Three hundred milliliters (ml) of purified, dried cyclohexane (99.5%, Phillips Petroleum) were introduced into a six-hundred milliliter stirred glass reactor. Air was removed from the reactor under vacuum and replaced by dry nitrogen. The reactor was equipped with an air driven stirrer, a pressure gauge, thermocouple, top surface inlet valve, dip tube feeder with valve, heating-mantle and variable controller and combination nitrogen/vacuum inlet with valve. Three ml of a 0.01M solution of bipyridyl in cyclohexane, 7.3 ml (90 mmol) of tetrahydrofuran freshly distilled from benzophenone ketyl and 1.8 ml (18 mmol) of purified isoprene were injected into the reactor. The temperature of the reactor and its contents was raised to 50° C. The solution was then titrated by addition of 1.6M butyl lithium until a persistent red color was obtained. Following this, 3.75 ml of 1.6M butyl lithium was injected into the reactor in order to initiate polymerization of the isoprene. The reaction was allowed to run for one hour, after which 47.5 g of purified butadiene were pressured into the reactor at a rate such that the reaction temperature did not exceed 70° C. After one hour, the reactor pressure had returned to its initial level and the formation of the second block of the copolymer was completed. Isoprene (1.8 ml, 18 mmol) was again injected into the reactor to allow for the formation of the third and final block of the triblock polymer. After one hour, 0.35 ml of acetic acid (4.5 mmol) were injected into the reactor to quench the triblock living anion. The color of the reaction mixture changed from a dark amber to colorless immediately. The mixture was cooled to room temperature, filtered through alumina/Celite, an anti-oxidant, Irganox 1076 from Ciba-Geigy (100 ppm based on dry polymer) was added and solvent was removed under reduced pressure to yield a triblock polymer of about 8400 molecular weight as a clear, colorless, viscous fluid. Infra-red analysis (Fourier Transform) showed the butadiene center block to possess 55% (1,2)- and 45% of (1,4)-microstructure.

EXAMPLE II (Isoprene-Butadiene-Isoprene Triblock Polymer)

This example is similar to that of Example 1, but the scale was increased to utilize a one gallon stainless steel pressure reactor.

1500 grams of purified, dried cyclohexane (99.5%, Phillips Petroleum) were introduced into a one gallon stirred stainless steel reactor. The reactor was equipped with a stirrer, pressure gauge, thermocouple, top surface inlet, dip tube feeder with valve, variably controlled heater and heat exchange coil. Following the addition of the solvent, 50 ml (0.614 mol) of tetrahydrofuran freshly distilled from benzophenone ketyl, 43.3 ml (0.433 mol) of purified isoprene and an additional 80 g of cyclohexane were pressured into the reactor. The temperature of the reactor and its contents was raised to 50° C. Butyl lithium (61.2 ml of 1.5M solution, 91.8 mmol) was pressured into the reactor in order to titrate impurities and initiate polymerization of the isoprene. The reaction was allowed to run for one hour, after which 1100 ml of purified butadiene (12.65 mol) were pumped into the reactor at a rate such that the reaction temperature did not exceed 60° C. Cooling water was passed through the heat exchanger during this process to aid in the control of temperature. The butadiene feed was complete within thirty minutes. One hour later, the formation of the second block of the copolymer was complete and isoprene (43.3 ml, 0.433 mol) in 50 g of cyclohexane was again pressured into the reactor to allow for the formation of the third and final block of the triblock polymer. After one hour, the reaction mixture was cooled and discharged into a vessel containing 5.2 ml of acetic acid (90.8 mmol) to quench the triblock living anion. The mixture was filtered through alumina/Celite, an anti-oxidant (100 ppm based on dry polymer) was added and the solvent was removed under reduced pressure to yield a triblock polymer of about 8200 molecular weight as a clear, colorless, viscous fluid. Infra-red analysis (Fourier-Transform) showed the butadiene center block to possess 56% (1,2)- and 44% of (1,4)-microstructure.

EXAMPLE III (Viscosity as a Function of Molecular Weight)

This example illustrates the relationship between the molecular weight of the triblock polymers prepared in the manner substantially the same as that of Examples I and II and their resulting bulk viscosities.

As is apparent from the data of FIG. 1, a linear relationship exists between the molecular weight of the unhydrogenated isoprene-butadiene-isoprene polymers prepared as in Examples I and II and the log of their room temperature bulk viscosities as measured using a Brookfield Engineering LVT viscometer operating at, for example, 0.6 rpm with spindle number 5.

EXAMPLE IV (Isoprene/Styrene-Butadiene-Isoprene/Styrene Triblock Polymer)

This example illustrates the preparation of a triblock polymer wherein the terminal blocks consist of isoprene-styrene copolymers. Incorporation of levels of styrene approximately comparable to those of isoprene into the end blocks is beneficial with certain methods of vulcanizing the final selectively hydrogenated triblock. 1400 grams of purified, dried cyclohexane (99.5%, Phillips Petroleulm) were introduced into a one gallon stirred stainless steel reactor. The reactor was equipped with a stirrer, pressure gauge, thermocouple, top surface inlet, dip tube feeder with valve, variably controlled heater and heat exchange coil. Following the addition of the solvent, 88 ml (1.08 mol) of tetrahydrofuran freshly distilled from benzophenone ketyl, 21.8 ml (0.218 mol) of purified isoprene, 41.5 ml of purified styrene (0.362 mol) and an additional 50 g of cyclohexane were pressured into the reactor. The temperature of the reactor and its contents was raised to 50° C. Butyl lithium (47.0 ml of 1.6M solution, 75.2 mmol) was then pressured into the reactor in order to titrate impurities and initiate polymerization of the isoprene. The reaction was allowed to run for one hour, after which 800 ml of purified butadiene (9.20 mol)

were pumped into the reactor at a rate such that the reaction temperature did not exceed 60° C. Cooling water was passed through the heat exchanger during this process to aid in the control of temperature. The butadiene feed was complete within thirty minutes. One hour later, the formation of the second block of the copolymer was complete and a mixture of isoprene (21.8 ml, 0.218 mol) and styrene (41.5 ml, 0.362 mol) in 50 g of cyclohexane was again pressured into the reactor to allow for the formation of the third and final block of the triblock polymer. After one hour, the reaction mixture was cooled and discharged into a vessel containing 4.3 ml of acetic acid (75.2 mmol) to quench the triblock living anion. The mixture was filtered through alumina/Celite, an anti-oxidant (100 ppm based on dry polymer) was added and solvent was removed under reduced pressure to yield a triblock polymer of about 8000 molecular weight as a clear, colorless viscous fluid. Infra-red analysis (Fourier Transform) showed the butadiene center block to possess 57% (1,2)- and 43% (1,4)-microstructure.

EXAMPLE V (Isoprene-Butadiene Random Copolymer)

This example illustrates the preparation of a random copolymer consisting of isoprene and butadiene wherein the isoprene proportion is completely analogous to that of the triblock material of Example I.

800 ml of purified, dried cyclohexane (99.5%, Phillips Petroleum) were introduced into a two liter stirred glass reactor. The reactor was purged several times with dry nitrogen. The reactor was equipped with an air driven stirrer, a pressure gauge, thermocouple, top surface inlet valve, dip tube feeder with valve, heat exchange coil and nitrogen inlet with valve. 5 ml of a 0.01M solution of bipyridyl in cyclohexane and 16.1 ml (198 mmol) of tetrahydrofuran freshly distilled form benzophenone ketyl were injected into the reactor. The reactor contents were titrated with 1.6M butyl lithium to a persistent red endpoint. The temperature of the reactor and its contents was raised to 50° C. and 8.3 ml of 1.6M butyl lithium (13.3 mmol) were added. A mixture of 13.3 ml of isoprene (0.133 mol) and 90.9 g of purified butadiene (1.68 mol) was then pressured into the reactor at a rate that allowed for maintaining a temperature of between 50° and 60° C. The feed was completed in about 20 minutes, after which the reaction was allowed to proceed for an additional hour. The contents were cooled and discharged into a vessel containing 0.53 ml of methanol (13 mmol) to quench the copolymer living anion. The color of the reaction mixture changed from a dark amber to colorless immediately. The mixture was filtered through alumina/Celite, an anti-oxidant (100 ppm based on dry polymer) was added and solvent was removed under reduced pressure to yield a random copolymer of about 7500 molecular weight as a clear, colorless, viscous fluid. Infra-red analysis (Fourier Transform) showed the butadiene portion to possess 60% (1,2)- and 40% (1,4)-microstructure. In general, the infra-red spectrum was essentially indistinguishable from that of the triblock material of Examples I and II.

EXAMPLE VI-COMPARATIVE (Low Molecular Weight Polybutadiene)

This example illustrates the preparation of a low molecular weight polybutadiene in a manner completely analogous to that of the random copolymer of Example V.

800 ml of purified, dried cyclohexane (99.5%, Phillips Petroleum) were introduced into a two liter stirred glass reactor. The reactor was purged several times with dry nitrogen. The reactor was equipped with an air driven stirrer, a pressure gauge, thermocouple, top surface inlet valve, dip tube feeder with valve, heat exchange coil and nitrogen inlet with valve. 5 ml of a 0.01M solution of bipyridyl in cyclohexane and 16.1 ml (198 mmol) of tetrahydrofuran freshly distilled from benzophenone ketyl were injected into the reactor. The reactor contents were titrated with 1.6M butyl lithium to a persistent red endpoint. The temperature of the reactor and its contents was raised to 50° C. and 8.3 ml of 1.6M butyl lithium (13.3 mmol) were added. Purified butadiene (100 g, 1.85 mol) was then pressured into the reactor at a rate that allowed for maintaining a temperature of between 50° and 60° C. The feed was complete in about 20 minutes, after which the reaction was allowed to proceed for an additional hour. The contents were cooled and discharged into a vessel containing 0.55 ml of methanol (13.5 mmol) to quench the polybutadienyl living anion. The color of the reaction mixture changed from a dark amber to colorless immediately. The mixture was filtered through alumina/Celite, an anti-oxidant (100 ppm based on dry polymer) was added and solvent was removed under reduced pressure to yield polybutadiene of about 7500 molecular weight as a clear, colorless, viscous fluid. Infra-red analysis (Fourier Transform) showed the polybutadiene to possess 45% (1,2)-and 55% (1,4)-microstructure. In general, the infra-red spectrum was essentially indistinguishable from that of the triblock material of Examples I and II.

EXAMPLE VII (Hydrogenation Catalyst Preparation)

This example illustrates the preparation of the selective hydrogenation catalyst used in subsequent examples.

In a clean, dry pressure bottle equipped with a magnetic stir bar. were placed 77.88 ml of pure, dry cyclohexane and 7.34 g of nickel (II) octoate (8% in mineral spirits, Mooney Chemical). The bottle was sealed with a septum and bottle cap, evacuated and refilled with dry nitrogen. The process was repeated several times. The mixture was then stirred vigorously and 14.40 ml of 1.73M triethylaluminum was added via syringe as quickly as practicable (about 15 seconds). Periodically, pressure was vented by means of a needle fitted with a valve. There was no evidence of heterogeneity in the final black reaction mixture. The catalyst solution nickel concentration was 0.1M and the molar ratio of aluminum to nickel was 3.6.

EXAMPLE VIII (Hydrogenation of Isoprene-Butadiene-Isoprene Block Copolymer)

This example illustrates the selective hydrogenation of the central polybutadiene block of an isoprene-butadiene-isoprene triblock polymer.

250 ml of cyclohexane in which was dissolved 23 g of triblock polymer made in the manner similar to that of Example I were purged of air by evacuation followed by the introduction of dry nitrogen. This amount of polymer contained 0.403 moles of polybutadiene unsaturation. To the polymer solution was added 25 ml of a hydrogenation catalyst solution comprised of triethylaluminum and nickel (II) octoate in a 3.6:1 ratio with a nickel concentration of 0.1M in cyclohexane. The resulting mixture was placed in a Parr hydrogenation apparatus and pressured to 50 psig hydrogen. The apparatus was vented and the process repeated twice more, after which the pressure was maintained at 50 psig of hydrogen. The temperature was raised to 50° C. and the mixture was agitated vigorously. Hydrogen was fed on demand in order to maintain 50 psig in the vessel and the flow rate was monitored by means of a mass flow meter. The progress of the hydrogenation process was monitored both by Fourier Transform infra-red spectroscopy and hydrogen flow rate. An infra-red spectrum obtained at the start of the process displayed the presence of primarily the butadiene unsaturation (peaks at 995, 968 and 910 wavenumbers). After thirty minutes, butadiene vinyl unsaturation (peaks at 995 and 910 wavenumbers) was gone, the trans-(1,4)-butadiene was significantly reduced (968 wavenumbers) and the isoprene vinylidene (888 wavenumbers) was very much in evidence. After ninety minutes, only the isoprene unsaturation remained. This final point corresponds to zero hydrogen flow. Upon completion of the selective hydrogenation process, the vessel was vented and the black reaction mixture was stirred in air with ammonium hydroxide and methanol stoichiometrically equivalent to the total catalyst metal content (11.5 mmol, 0.7 ml concentrated ammonia and 0.5 ml methanol). Within several hours, the mixture had changed to a dark green color indicative of oxidized nickel. The mixture was filtered through alumina/Celite and an anti-oxidant was added in the amount equivalent to 100 ppm based on the dry polymer weight. Solvent was then removed under reduced pressure to yield the product as a clear, colorless, viscous fluid.

EXAMPLE IX (Viscosity as a Function of Molecular Weight of Hydrogenated Triblock Copolymer)

This example illustrates the relationship between the molecular weight of the selectively hydrogenated triblock polymers prepared in the manner of Example VIII and their resulting bulk viscosities.

Figure 2:
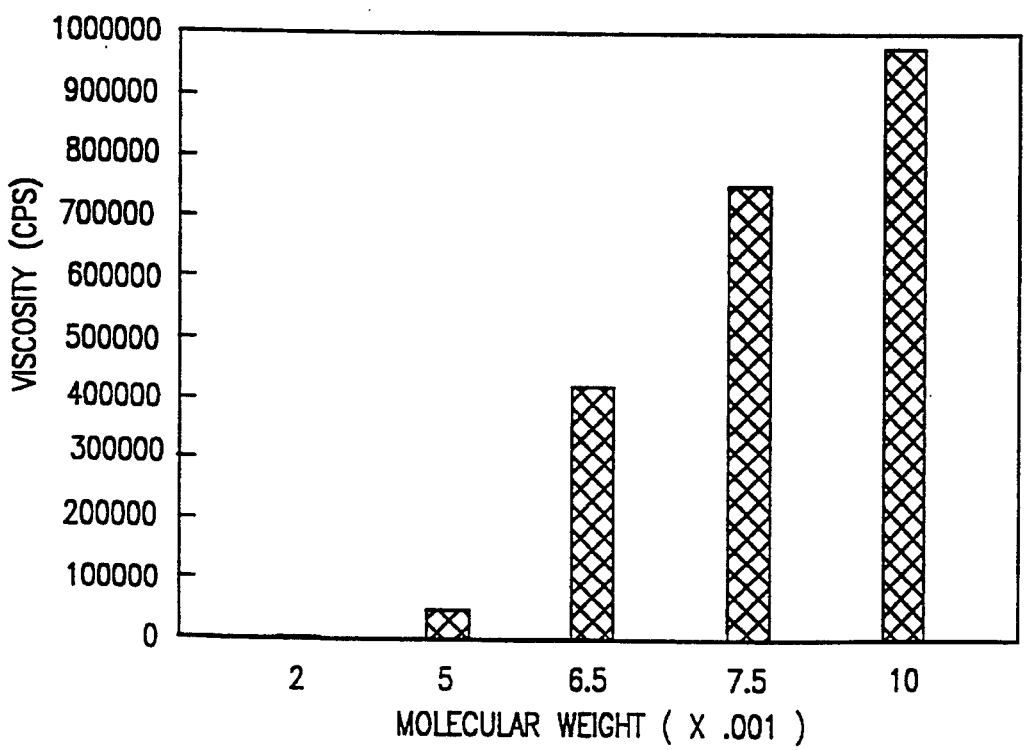
FIG. 2 shows the relationship of viscosity as a function of molecular weight for the hydrogenated isoprene-butadiene-isoprene triblock polymer of this invention.

As is apparent in FIG. 2, a monotonic increase in room temperature bulk viscosity is observed as the molecular weight of the selectively hydrogenated triblock polymers is increased. In all cases, a Brookfield Engineering LVT viscometer operating at, for example 0.6 rpm with spindle number 5 was used. Surprisingly, however, even at a molecular weight of ten thousand g/mol (Mn=Mw) the bulk viscosity does not exceed one million centipoises.

| Triblock Molecular Weight | | | | |
|---|---|---|---|---|
| 2000 | 5000 | 6500 | 7500 | 10000 |
| Bulk Viscosity (cps) | | | | |
| 8500 | 54700 | 424000 | 745000 | 976000 |

EXAMPLE X (Hydrogenation of Isoprene/Styrene-Butadiene-Isoprene/Styrene Triblock Polymer)

This example illustrates the selective hydrogenation of the central polybutadiene block of a triblock polymer wherein the terminal blocks consist of isoprene-styrene copolymers.

The process was carried out in a manner completely analogous to that of Example VIII to give a material in which only the isoprene unsaturation remained as evidenced by Fourier Transform infra-red spectroscopy.

EXAMPLE XI (Hydrogenation of Random Isoprene-Butadiene Copolymer)

This example illustrates the selective hydrogenation of the butadiene portion of a random copolymer of isoprene-butadiene prepared as in Example V.

The process was carried out in a manner completely analogous to that of Example VIII to give a material in which only the isoprene unsaturation remained as evidenced by Fourier Transform infra-red spectroscopy.

EXAMPLE XII (Hydrogenation of Low MW Polybutadiene)

This example illustrates the selective partial hydrogenation of a low molecular weight polybutadiene prepared as in Example VI.

250 ml of cyclohexane in which was dissolved 30 g of polybutadiene prepared in Example VI were purged of air by evacuation followed by introduction of dry nitrogen. This amount of polymer contained 0.556 moles of unsaturation. To the polymer solution was added 15 ml of a hydrogenation catalyst solution analogous to that of Example VIII. The resulting mixture was placed in a Parr hydrogenation apparatus and pressured to 50 psig hydrogen. The apparatus was vented and the process repeated twice more, after which the pressure was maintained at 50 psig of hydrogen. The mixture was agitated vigorously and hydrogen was fed on demand in order to maintain 50 psig pressure in the vessel. The progress of the hydrogenation process was monitored both by Fourier Transform infra-red spectroscopy and hydrogen flow rate as indicated by a mass flow meter. After twenty-five minutes, the hydrogen flow rate had reached a level that indicated that most of the hydrogenation was complete. The process was halted and an infra-red spectrum showed only the presence of trans-(1,4)-polybutadiene unsaturation at a level comparable to that of isoprene unsaturation levels of selectively hydrogenated isoprene-butadiene-isoprene triblock polymers prepared as in Example VIII. The vessel was vented and the black reaction mixture was stirred in air with ammonium hydroxide and methanol stoichoimetrically equivalent to the total catalyst metal content (6.9 mmol, 0.4 ml concentrated ammonia and 0.3 ml methanol). Within several hours the mixture had changed to a dark green color indicative of oxidized nickel. The mixture was filtered through alumina/Celite and an anti-oxidant was added in an amount equivalent to 100 ppm based on dry polymer weight. The solvent was then removed under reduced pressure to yield the product which was a clear, colorless, viscous fluid.

EXAMPLE XIII (Vulcanization of Hydrogenated Isoprene-Butadiene-Isoprene Triblock)

This example illustrates the low temperature vulcanization (cure) of a selectively hydrogenated low molecular weight isoprene-butadiene-isoprene triblock polymer into a solid rubber using the quinone dioxime (GMF) cure.

The ingredients listed below were mixed thoroughly without heating either by hand or in a Brabender mixer to a uniform consistency. The resulting paste was placed in a Teflon mold with dimensions of 3"×3"×0.25" and cured in a Carver press for one hour at 50° C. and 6000 psi pressure. Subsequently, the sample was removed from the mold and allowed to age for a period of at least three hours at 50° C. The resulting solid rubber was non-tacky, elastic and displayed tensile strength and elongation values at break of 350 psi and 200% respectively.

| Mix Recipe | Parts |
| --- | --- |
| Triblock Polymer | 100.0 |
| GMF (quinone dioxime) | 11.0 |
| N-Chlorosuccinimide | 17.2 |
| Zinc Oxide | 7.6 |

EXAMPLE XIV (Rubber Properties as Function of Molecular weight)

This example illustrates the relationship between selectively hydrogenated triblock polymer molecular weight and final cured rubber properties. The cure method as described in Example XIII was employed with the addition of silica as an inert filler at a level of 50 parts to cure triblock polymers of isoprene-butadiene-isoprene prepared in the manner substantially the same as that of Example VII. The results are summarized below and in FIG. 3.

Figure 3:
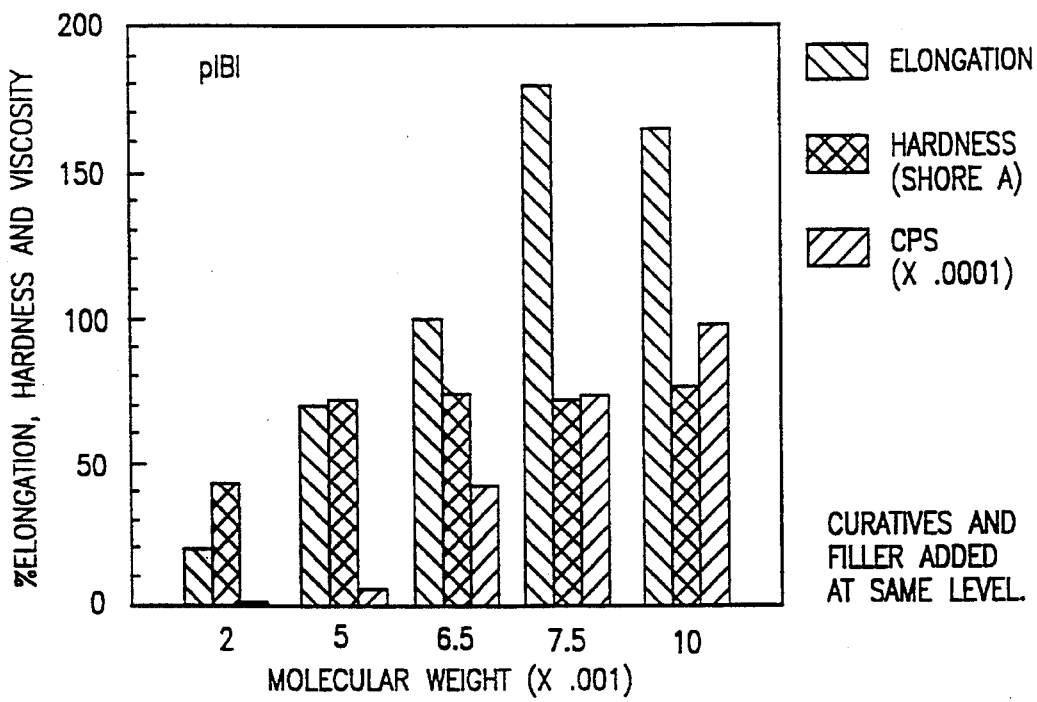
FIGS. 3 and 4 show properties of the cured selectively hydrogenated isoprene-butadiene-isoprene polymers of this invention as a function of molecular weight thereof.

As shown in FIG. 3, for the range of molecular weights examined (2,000 to 10,000 g/mol), a maximum percent elongation value of 180% at break was observed for the 7,500 molecular weight selectively hydrogenated triblock polymer. The 10,000 molecular weight material displayed a similar but slightly inferior value and the materials of lower molecular weight were clearly inferior with respect to cured properties. For comparison, the uncured triblock bulk viscosities are included in the data.

| Mix Recipe: | Parts | | | | |
| --- | --- | --- | --- | --- | --- |
| Triblock Polymer | 100.0 | | | | |
| GMF | 14.4 | | | | |
| N-Chlorosuccinimide | 22.4 | | | | |
| Zinc Oxide | 10.0 | | | | |
| Silica | 50.0 | | | | |
| Physical Properties: | | | | | |
| Molecular Weight | 2,000 | 5,000 | 6,500 | 7,500 | 10,000 |
| Bulk Viscosity (cps) | 8,500 | 54,700 | 424,000 | 745,000 | 976,000 |
| % Elongation | 20 | 75 | 100 | 180 | 165 |

EXAMPLE XV (Cured Rubber Properties as Function of Hydrogenated Polymer MW)

This example illustrates the relationship between selectively hydrogenated triblock polymer molecular weight and final cured rubber properties. The cure method as described in Example XIII was employed with the adjustment of the curative levels to the isoprene unsaturation levels for the appropriate molecular weight. The triblock polymers were made from isoprene-butadiene-isoprene in the manner substantially the same as that of Example VII. The results are summarized below and in FIG. 4.

Figure 4:
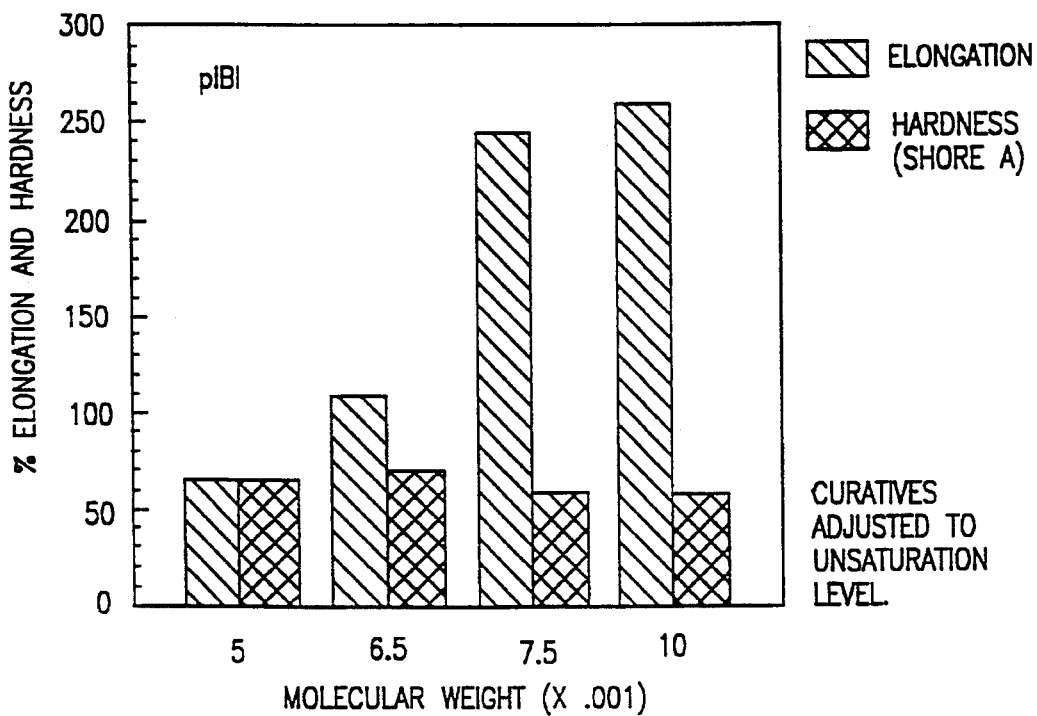

As shown in FIG. 4, for the range of molecular weights examined (5,000 to 10,000 g/mol), a maximum percent elongation value of greater than 250% at break was observed for the materials above 7,500 molecular weight. The 10,000 molecular weight material displayed slightly better elongation and the lower molecular weight polymers were clearly inferior with elongations at break of 100% and less.

| Molecular Weight | 5,000 | 6,500 | 7,500 | 10,000 |
| --- | --- | --- | --- | --- |
| Mix Recipe: | | | | |
| Polymer | 100.0 | 100.0 | 100.0 | 100.0 |
| GMF | 19.6 | 14.4 | 12.4 | 9.4 |
| N-Chlorosuccinimide | 25.2 | 22.4 | 19.4 | 14.6 |
| Zinc Oxide | 13.2 | 10.0 | 8.6 | 6.6 |
| Physical Properties % Elongation | 65 | 109 | 245 | 262 |

EXAMPLE XVI (Star Branched Polymers)

This example illustrates the preparation of an isoprene-butadiene-isoprene triblock living polymer that is subsequently coupled to yield branched materials containing two arms (a pentablock), three arms (Y-shaped), four arms (plus-shaped), etc. The method is similar to that of Example I, but a fractional equivalent of quenching reagent containing multiple sites to react with the polymer living anion, such as silicon tetrachloride, was employed instead of acetic acid. For example, one-fourth of an equivalent of silicon tetrachloride was used based on the amount of n-butyl lithium employed in the polymerization.

The polymers prepared were obtained as colorless fluids with viscosities comparable to the parent triblock polymer, i.e., the materials are still liquids despite their relatively high molecular weights.

| Quenching Reagent | Polymer Obtained | Bulk Viscosity (cps) |
| --- | --- | --- |
| Trichlorosilane | Y-shaped, 25500 g/mol | 569,000 |
| Silicon Tetrachloride | +-shaped, 34000 g/mol | 254,000 |
| Unhydrogenated 8500 MW Triblock from Example III: | | 178,000 |

EXAMPLE XVII (Star Branched Polymers)

This example illustrates the preparation of an isoprene-butadiene diblock living polymer that is subsequently coupled to yield branched materials containing two arms (a triblock), three arms (Y-shaped), four arms (plus-shaped), etc. The method is similar to that of Example XVI, but quenching of the living anion is performed after the formation of the second polymer block i.e., the polyisoprene-butadienyl anion. The material obtained had isoprene blocks only on the ends of the individual branches and not at their junction.

EXAMPLE XVIII (Hydrogenation of Star-Branched Polymers)

This example illustrates the selective hydrogenation of the butadiene blocks of the branched materials of Examples XVI and XVII.

The process was carried out in a manner analogous to that of Example VIII to give materials in which only the isoprene unsaturation remained as evidenced by Fourier Transform infra-red spectroscopy.

EXAMPLE XIX (Properties of Hydrogenated Polymers)

This example illustrates the relationship between the degree of branching of selectively hydrogenated isoprene-butadiene-isoprene polymers with approximately the same distance between crosslinks, $M_C$ of 8500, and the molecular weight and final cured rubber properties. The cure method as described in Example XIII was employed. The branched materials cured significantly faster at the same curatives level to rubbers of somewhat superior performance. All three samples of this Example were prepared from the same mix recipe summarized below.

| Mix Recipe: | | Parts | |
| --- | --- | --- | --- |
| Triblock Polymer | | 100.0 | |
| GMF | | 11.0 | |
| N-Chlorosuccinimide | | 17.2 | |
| Zinc Oxide | | 7.6 | |
| Uncured Molecular Weight | 8400 | 25500 | 34000 |
| Cured Physical Properties | | | |
| Approximate $M_c$ | 8400 | 8500 | 8500 |
| % Elongation | 202 | 201 | 266 |
| Tensile (psi) | 329 | 408 | 421 |
| Shore A Hardness | 64 | 62 | 58 |

It will be apparent to those skilled in the art that the specific embodiments discussed above can be successfully repeated with ingredients equivalent to those generically or specifically set forth above and under variable process conditions.

From the foregoing specification, one skilled in the art can readily ascertain the essential features of this invention and without departing from the spirit and scope thereof can adapt it to various diverse applications.

We claim:

1. A liquid random copolymer comprising at least one polymerized conjugated diene of formula (1) and at least one polymerized conjugated diene of formula (3), wherein:

the diene of formula (1) has at least five (5) carbon atoms and the following formula

where $R^1$–$R^6$ are each hydrogen or a hydrocarbyl group, provided that at least one of $R^1$–$R^6$ is a hydrocarbyl group and provided that the structure of the residual double bond in the polymerized diene of formula (1) has the following formula

wherein $R^I$, $R^{II}$, $R^{III}$ and $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups;

the diene of formula (3) is different from the diene of formula (1), it has at least four (4) carbon atoms and the following formula

wherein $R^7$–$R^{12}$ are each hydrogen or a hydrocarbyl group, provided that the structure of the residual double bond in the polymerized diene of formula (3) has the following formula

wherein $R^a$, $R^b$, $R^c$ and $R^d$ are each hydrogen (H) or a hydrocarbyl group, provided that one of $R^a$ or $R^b$ is hydrogen, one of $R^c$ or $R^d$ is hydrogen, and at least one of $R^a$, $R^b$, $R^c$ or $R^d$ is a hydrocarbyl group; and wherein the conjugated diene of formula (1) is present in the copolymer in the amount of about 1.0 to about 25% by mole, and the conjugated diene of formula (3) is present in the copolymer in the amount of about 75 to about 99% by mole, said copolymer being selectively hydrogenated, so that the polymerized conjugated diene of formula (3) is substantially completely hydrogenated and thereby contains substantially none of the original unsaturation and the polymerized conjugated diene of formula (1) retains a sufficient amount of its original unsaturation to vulcanize said copolymer.

2. A copolymer of claim 1 wherein, after the hydrogenation reaction, the Iodine Number for the polymerized conjugated diene of formula (1) is about 20 to about 100% of the Iodine Number for the polymerized conjugated diene of formula (1) prior to the hydrogenation reaction.

3. A copolymer of claim 2 wherein, after the hydrogenation reaction, the Iodine Number for the polymerized conjugated diene of formula (1) is about 50 to about 100% of the Iodine Number for the polymerized conjugated diene of formula (1) prior to the hydrogenation reaction.

4. A copolymer of claim 2 wherein, after the hydrogenation reaction, the Iodine Number for the polymerized conjugated diene of formula (1) is about 100% of the Iodine Number for the polymerized conjugated diene of formula (1) prior to the hydrogenation reaction.

5. A copolymer of claim 4 wherein the Iodine Number for the polymerized conjugated diene of formula (3) after the hydrogenation reaction is about 0 to about 10% of the Iodine Number prior to the hydrogenation reaction.

6. A copolymer of claim 5 wherein the Iodine Number for the polymerized conjugated diene of formula (3) after the hydrogenation reaction is about 0 to about 0.5% of the Iodine Number prior to the hydrogenation reaction.

7. A copolymer of claim 5 wherein the Iodine Number for the polymerized conjugated diene of formula (3) after the hydrogenated reaction is about 0 to about 0.2% of the Iodine Number prior to the hydrogenation reaction.

8. A copolymer of claim 7 wherein the conjugated diene of formula (1) is isoprene, 2,3-dimethyl-butadiene, 2-methyl-1,3-pentadiene, myrcene, 2-methyl-1,3-pentadiene, 3-methyl-1,3-pentadiene, 4-methyl-1,3-pentadiene, 2-phenyl-1,3-butadiene, 2-phenyl-1,3-pentadiene, 3-phenyl-1,3-pentadiene, 2,3-dimethyl-1,3-pentadiene, 4-methyl-1,3-pentadiene, 2-hexyl-1,3-butadiene, 3-methyl-1,3-hexadiene, 2-benzyl-1,3-butadiene, 2-p-tolyl-1,3-butadiene or mixtures thereof.

9. A copolymer of claim 8 wherein the diene of formula (1) is isoprene, myrcene or 2-methyl-1,3-pentadiene.

10. A copolymer of claim 9 wherein the conjugated diene of formula (1) is isoprene.

11. A copolymer of claim 10 wherein the diene of formula (3) is 1,3-butadiene, 1,3-pentadiene, 2,4-hexadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene or mixtures thereof.

12. A copolymer of claim 11 wherein the diene of formula (3) is 1,3-butadiene, 1,3-pentadiene, 2,4-hexadiene or 1,3-hexadiene.

13. A copolymer of claim 12 wherein the conjugated diene of formula (3) is 1,3-butadiene.

14. A copolymer of claim 13 comprises about 1.0 to about 10% by mole of the conjugated diene of formula (1) and about 90 to about 99% by mole of the conjugated diene of formula (3).

15. A copolymer of claim 14 wherein the polymerized 1,3-butadiene, prior to hydrogenation, is a mixture of 1,4- and 1,2-units.

16. A copolymer of claim 15 wherein the polymerized 1,3-butadiene, prior to hydrogenation, has at least 25% wt. of the 1,2-units.

17. A copolymer of claim 16 wherein the polymerized 1,3-butadiene, prior to hydrogenation, has about 30 to about 90% wt. of the 1,2-units and about 10 to about 70% wt. of the 1,4-units.

18. A copolymer of claim 16 wherein the polymerized conjugated diene of formula (3), prior to hydrogenation, has about 45 to about 65% wt. of the 1,2-units and about 55 to about 35% wt. of the 1,4-units.

19. A liquid, random copolymer comprising:
about 0.3 to about 15% by mole of at least one aryl-substituted olefin;
about 1.0 to about 25% by mole of at least one conjugated diene having at least five (5) carbon atoms and the following formula

wherein
$R^1$–$R^6$ are each hydrogen or a hydrocarbyl group, provided that at least one of $R^1$–$R^6$ is a hydrocarbyl group and provided that the structure of the residual double bond in the polymerized block I has the following formula

wherein
$R^I$, $R^{II}$, $R^{III}$ $R^{IV}$ are each hydrogen or a hydrocarbyl group, provided that either both $R^I$ and $R^{II}$ are hydrocarbyl groups or both $R^{III}$ and $R^{IV}$ are hydrocarbyl groups;
and the remainder of at least one conjugated diene, different from the diene of formula (1), having at least four (4) carbon atoms and the following formula

wherein
$R^7$–$R^{12}$ are each hydrogen or a hydrocarbyl group, provided that the structure of the residual double bond in the polymerized diene of formula (3) has the following formula

wherein
$R^a$, $R^b$, $R^c$ and $R^d$ are each hydrogen (H) or a hydrocarbyl group, provided that one of $R^a$ or $R^b$ is hydrogen, one of $R^c$ or $R^d$ is hydrogen and at least one of $R^a$, $R^b$, $R^c$ or $R^d$ is a hydrocarbyl group.

20. A copolymer of claim 19 wherein the aryl-substituted olefin has the formula

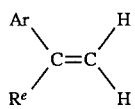

wherein
Ar is phenyl, alkyl-substituted phenyl, naphthyl, or alkyl-substituted naphthyl and $R^e$ is hydrogen, methyl, ethyl, propyl, butyl or aryl.

21. A copolymer of claim 20 which is selectively hydrogenated so that the polymerized conjugated diene of formula (3) is substantially completely hydrogenated and thereby contains substantially none of the original unsaturation, while the polymerized conjugated diene of formula (1) retains a sufficient amount of its original unsaturation to vulcanize the copolymer.

22. A copolymer of claim 21 wherein the aryl-substituted olefin is styrene, 2-phenyl-alpha olefin, alkylated styrene, vinyl naphthalene, or alkylated vinyl naphthalene and the conjugated diene of formula (1) is isoprene, 2,3-dimethyl-butadiene, 2-methyl-1,3-pentadiene, myrcene, 2-methyl-1,3-pentadiene, 3-methyl-1,3-pentadiene, 4-methyl-1,3-pentadiene, 2-phenyl-1,3-butadiene, 2-phenyl-1,3-pentadiene, 3-phenyl-1,3-pentadiene, 2,3-dimethyl-1,3-pentadiene, 4-methyl-1,3-pentadiene, 2-hexyl-1,3-butadiene, 3-methyl-1,3-hexadiene, 2-benzyl-1,3-butadiene, 2-p-tolyl-1,3-butadiene or mixture thereof.

23. A copolymer of claim 22 wherein the diene of formula (1) is isoprene, myrcene or 2-methyl-1,3-pentadiene.

24. A copolymer of claim 23 wherein the aryl-substituted olefin is styrene, alpha-methyl styrene or 1,1-diphenyl ethylene and the diene of formula (1) is isoprene.

25. A copolymer of claim 24 wherein the diene of formula (3) is 1,3-butadiene, 1,3-pentadiene, 2,4-hexadiene, 1,3-hexadiene, 1,3-heptadiene, 2,4-heptadiene, 1,3-octadiene, 2,4-octadiene, 3,5-octadiene, 1,3-nonadiene, 2,4-nonadiene, 3,5-nonadiene, 1,3-decadiene, 2,4-decadiene, 3,5-decadiene or mixtures thereof.

26. A copolymer of claim 25 wherein the diene of formula (3) is 1,3-butadiene, 1,3-pentadiene, 2,4-hexadiene or 1,3-hexadiene.

27. A copolymer of claim 26 wherein the diene of formula (3) is 1,3-butadiene and the aryl-substituted olefin is styrene.

* * * * *